United States Patent
Newman et al.

(10) Patent No.: US 12,097,234 B2
(45) Date of Patent: Sep. 24, 2024

(54) EXTRACT CONTAINING OLEANDRIN AND METHOD OF PRODUCTION THEREOF

(71) Applicant: PHOENIX BIOTECHNOLOGY, INC., San Antonio, TX (US)

(72) Inventors: Robert A. Newman, St. Helena Island, SC (US); Otis C. Addington, San Antonio, TX (US); Richard J. Obiso, Christiansburg, VA (US)

(73) Assignee: PHOENIX BIOTECHNOLOGY, INC., San Antonio, TX (US)

( * ) Notice: Subject to any disclaimer, the term of this patent is extended or adjusted under 35 U.S.C. 154(b) by 0 days.

(21) Appl. No.: 18/058,463

(22) Filed: Nov. 23, 2022

(65) Prior Publication Data

US 2023/0158093 A1    May 25, 2023

Related U.S. Application Data

(63) Continuation of application No. PCT/US2021/033176, filed on May 19, 2021, which is a continuation-in-part of application No. PCT/US2021/022800, filed on Mar. 17, 2021, which is a continuation-in-part of application No. PCT/US2020/042009, filed on Jul. 14, 2020, which is a continuation-in-part of application No. 16/895,920, filed on Jun. 8, 2020, now Pat. No. 10,729,735.

(60) Provisional application No. 63/159,242, filed on Mar. 10, 2021, provisional application No. 63/059,776, filed on Jul. 31, 2020, provisional application No. 63/057,727, filed on Jul. 28, 2020, provisional application No. 63/051,576, filed on Jul. 14, 2020, provisional application No. 63/042,656, filed on Jun. 23, 2020, provisional application No. 63/034,800, filed on Jun. 4, 2020, provisional application No. 63/029,530, filed on May 24, 2020.

(51) Int. Cl.
  *A61K 36/51*    (2006.01)
  *A61K 47/10*    (2017.01)
  *A61P 31/14*    (2006.01)

(52) U.S. Cl.
  CPC .............. *A61K 36/51* (2013.01); *A61K 47/10* (2013.01); *A61P 31/14* (2018.01)

(58) Field of Classification Search
  CPC .......... A61K 36/51; A61K 47/10; A61K 8/00; A61K 9/006; A61K 9/107; A61K 9/2054; A61K 9/4858; A61K 9/4891; A61K 47/14; A61K 2236/00; A61K 31/704; A61K 31/7048; A61K 36/24; A61K 31/56
  See application file for complete search history.

(56) References Cited

U.S. PATENT DOCUMENTS

| | | | |
|---|---|---|---|
| 3,833,472 | A | 9/1974 | Yamauchi |
| 4,554,170 | A | 11/1985 | Panzer |
| 4,968,787 | A | 11/1990 | Nada |
| 5,135,745 | A | 7/1992 | Ozel |
| 5,236,132 | A | 8/1993 | Rowley |
| 5,598,979 | A | 2/1997 | Rowley |
| 5,837,831 | A | 11/1998 | Grunning |
| 5,869,060 | A | 2/1999 | Woon et al. |
| 6,517,015 | B2 | 2/2003 | Rowley |
| 6,565,897 | B2 | 5/2003 | Selvaraj |
| 6,715,705 | B2 | 4/2004 | Rowley |
| 7,402,325 | B2 | 7/2008 | Addington |
| 8,187,644 | B2 | 5/2012 | Addington |
| 8,367,363 | B2 | 1/2013 | Addington |
| 8,394,434 | B2 | 2/2013 | Addington |
| 8,481,086 | B2 | 6/2013 | Addington |
| 9,220,778 | B2 | 12/2015 | Addington |
| 9,358,293 | B2 | 5/2016 | Addington |
| 9,494,589 | B2 | 10/2016 | Addington et al. |
| 9,846,156 | B2 | 11/2017 | Addington et al. |
| 9,877,979 | B2 | 1/2018 | Addington et al. |
| 10,596,186 | B2 | 3/2020 | Newman et al. |
| 2002/0114852 | A1 | 8/2002 | Selvaraj |
| 2004/0082521 | A1 | 4/2004 | Singh |
| 2005/0112059 | A1 | 5/2005 | Newman |
| 2006/0205679 | A1 | 9/2006 | Streeper |
| 2011/0172172 | A1 | 7/2011 | Addington |
| 2016/0243143 | A1 | 8/2016 | Addington |
| 2020/0138774 | A1 | 5/2020 | Sorbo et al. |

FOREIGN PATENT DOCUMENTS

| | | | |
|---|---|---|---|
| KR | 20180060726 A | 6/2018 | |
| WO | WO-2012129683 A1 * | 10/2012 | ............. A61K 36/15 |

OTHER PUBLICATIONS

Hamburger et al. ("Supercritical carbon dioxide extraction of selected medicinal plants—effects of high pressure and added ethanol on the yield of extracted substances", Phytochem. Anal. (2004), 15, pp. 46-54).

(Continued)

*Primary Examiner* — Robert A Wax
*Assistant Examiner* — Quanglong N Truong
(74) *Attorney, Agent, or Firm* — INNOVAR, L.L.C.; Rick Matos

(57) ABSTRACT

A subcritical liquid extraction process for the production of oleandrin or oleandrin-containing extract is provided. The process provides improvements over other methods of preparing oleandrin-containing extract. The extract, pharmaceutical compositions, dosage forms and nutraceutical compositions comprising oleandrin or said extract are provided. Methods of treating diseases, disorders or conditions that are therapeutically responsive to oleandrin are also provided.

29 Claims, 3 Drawing Sheets

(56) References Cited

OTHER PUBLICATIONS

Pathak S., et al. ("Anvirzel, an extract of Nerium oleander, induces cell death in human but not murine cancer cells" In Anticancer Drugs. Jul. 2000; 11(6):455-63).
Raventos M, et al. ("Application and Possibilities of Supercritical CO2 Extraction in Food Processing Industry: An Overview" in Food Sci. Tech. Int. vol. 8 (5) (2002) 269-284).
Erdemoglu et al. ("Antiinflammatory and antinociceptive activity assessment of plants used as remedy in Turkish fold medicine" in J. Ethnopharmacol. (Nov. 2003) 89(1), 123-129).
Adome et al. ("The cardiotonic effect of the crude ethanolic extract of Nerium oleander in the isolated guinea pig hearts" in Afr. Health Sci. (Aug. 2003) 3(2), 77-86).
El Shazly et al. ("Toxic effect of ethanolic extract of Nerium oleander [apocynaceae] levels against different developmental stages of muscin stabulans [dipteramuscidae]" in J. Egypt Soc. Parasitol. (1996), Aug. 26(2), 461-473).
Begum et al. ("Bioactive cardenolides from the leaves of Nerium oleander" in Phytochemistry (Feb. 1999) 50(3), 435-438).
Zia et al. ("Studies on the constituents of the leaves of Nerium oleander on behavior pattern in mice" in J. Ethnolpharmacol. (Nov. 1995) 49(1), 33-39).
Vlasenko et al. ("Extracting digitoxin, oleandrin and lanatoside with organic solvents" in Farmatsiia. (Sep.-Oct. 1972) 21(5), 46-47).
Yamauchi et al. ("Cardiac glycosides of the leaves of Nerium odorum", Phytochemistry (1975), 14, 1379-1382).
Siddiqui et al. ("Oleanderol, A new Pentacycylic Triterpene from the Leaves of Nerium Oleander" in Journal of Natural Products, vol. 51. No. 2, pp. 229-233, Mar.-Apr. 1988).
Turkmen et al. ("An HPTLC method for the determination of oleandrin in Nerium plant extracts and its application to forensic toxicology" in J. Planar Chroma. (2013), 26(3), 279-283).
Fartyal et al. ("Bioactivity of crude extracts of Nerium oleander Linn. extracted in polar and nonpolar solvents" in J. Sci. Innov. Res. (2014), 3(4), 426-432).

\* cited by examiner

Counts vs Acquisition Time (min)

+TIC Scan 3 Ole Supercritical Ext 1 d10 + 10 ppm IS Split 10.d

Counts vs Acquisition Time (min)

Time (min)

EXTRACT CONTAINING OLEANDRIN AND METHOD OF PRODUCTION THEREOF

CROSS-REFERENCE TO RELATED APPLICATIONS

The present application is a continuation of PCT/US2021/033176 filed May 19, 2021, which is a continuation-in-part of PCT/US2021/022800 filed Mar. 17, 2021, which claims the priority of 63/159,242 filed Mar. 10, 2021, 63/059,776 filed Jul. 31, 2020, and 63/057,727 filed Jul. 28, 2020, and said PCT/US2021/022800 is a continuation-in-part of PCT/US2020/042009 filed Jul. 14, 2020, which claims the benefit of 63/051,576 filed Jul. 14, 2020, 63/042,656 filed Jun. 23, 2020, 63/034,800 filed Jun. 4, 2020, 63/029,530 filed May 24, 2020, and said PCT/US2020/042009 is a continuation-in-part of Ser. No. 16/895,920 filed Jun. 8, 2020, now U.S. Ser. No. 10/729,735 issued Aug. 4, 2020, the entire disclosures of which are hereby incorporated by reference.

FIELD OF THE INVENTION

The present invention concerns an improved method for the preparation of an extract comprising oleandrin. The invention also provides an improved oleandrin-containing composition comprising at least two different oleandrin-containing extracts. Pharmaceutical compositions and nutraceutical compositions containing the same are also provided. Methods of use for the treatment of cardiac glycoside-responsive diseases, conditions or disorders are also provided.

BACKGROUND OF THE INVENTION

There is no suitable large-scale chemical synthetic process for production of oleandrin; therefore, it is produced primarily by extraction from plant material, which is optionally followed by isolation from other components of the extract and then purification.

*Nerium oleander*, a member of the *Nerium* species, is an ornamental plant widely distributed in subtropical Asia, the southwestern United States, and the Mediterranean. Its medical and toxicological properties have long been recognized primarily because of oleandrin, which has been proposed for use, for example, in the treatment of hemorrhoids, ulcers, leprosy, snake bites, neurological disorders, cancer, tumor, excessive cell proliferation, neurodegeneration, Alzheimer's disease, Parkinson's disease, stroke, neurological disorders, Huntington's disease, inflammation, and viral infection. The neuroprotective activity of oleandrin is disclosed in WO 2011085307 A1, U.S. Pat. No. 8,481,086 B2, U.S. Pat. No. 9,220,778 B2, U.S. Pat. No. 9,358,293 B2, U.S. Pat. No. 9,877,979 B2, and U.S. Ser. No. 10/383,886 B2. The anticancer (anti-excessive cell proliferation) activity oleandrin is disclosed in WO 2007016176A2, WO 2009064657 A1, U.S. Pat. No. 7,402,325 B2, U.S. Pat. No. 8,187,644 B2, U.S. Pat. No. 8,394,434 B2, U.S. Pat. No. 8,367,363 B2, U.S. Pat. No. 9,494,589 B2, and U.S. Pat. No. 9,846,156 B2. The antiviral activity of oleandrin is disclosed in U.S. Ser. No. 10/596,186, WO 2018/053123A1, and WO2019/055119A1. Zibbu et al. (J. Chem. Pharm. Res. (2010), 2(6), 351-358) provide a brief review on the chemistry and pharmacological activity of *Nerium oleander*.

Extraction of components from plants of *Nerium* species has traditionally been carried out using boiling water, supercritical fluid, or organic solvent.

ANVIRZEL™ (U.S. Pat. No. 5,135,745 to Ozel) contains the concentrated form or powdered form of the hot-water extract of *Nerium oleander*. Muller et al. (*Pharmazie*. (1991) September 46(9), 657-663) disclose the results regarding the analysis of a water extract of *Nerium oleander*. The extraction of the plant *Nerium oleander* involves slicing the leaves, cooking the sliced leaves and stems of the plant in water for 2-3 hours and filtering off the residues. The mixture is heated again. The aqueous extract reportedly contains several polysaccharides with molecular weights varying from 2 KD to 30 KD, oleandrin and oleandrigenin, odoroside and neritaloside. They report that the polysaccharide present is primarily galacturonic acid. Other saccharides include rhamnose, arabinose and galactose. Other saccharides include rhamnose, arabinose and galactose. Polysaccharide content and individual sugar composition of polysaccharides within the hot water extract of *Nerium oleander* have also been reported by Newman et al. (*J. Herbal Pharmacotherapy*, (2001) vol 1, pp. 1-16). Compositional analysis of ANVIRZEL™, the hot water extract, was described by Newman et al. (*Anal. Chem.* (2000), 72(15), 3547-3552). U.S. Pat. No. 5,869,060 to Selvaraj et al. pertains to extracts of *Nerium* species and methods of production. To prepare the extract, plant material is placed in water and boiled. The crude extract is then separated from the plant matter and sterilized by filtration. The resultant extract can then be lyophilized to produce a powder. U.S. Pat. No. 6,565,897 (U.S. Pregrant Publication No. 20020114852 and PCT International Publication No. WO 2000/016793 to Selvaraj et al.) discloses a hot-water extraction process for the preparation of a substantially sterile water extract. Ishikawa et al. (J. Nutr. Sci. Vitaminol. (2007), 53, 166-173) discloses a hot water extract of *Nerium oleander* and fractionation thereof by liquid chromatography using mixtures of chloroform, methanol, and water. They also report that extracts of the leaves of *N. oleander* have been used to treat Type II diabetes. US20060188585 published Aug. 24, 2006 to Panyosan discloses a hot water extract of *N. oleander*. U.S. Ser. No. 10/323,055 issued Jun. 18, 2019 to Smothers discloses a method of extracting plant material with aloe and water to provide an extract comprising aloe and cardiac glycoside. US20070154573 published Jul. 5, 2007 to Rashan et al. discloses a cold-water extract of *Nerium oleander* and its use. Methods to enhance the relative content of oleandrin from plant material are therefore warranted. While hot water extracts of *Nerium oleander* may provide oleandrin and related cardiac glycosides in relatively low yield, an improved method for obtaining a concentrated form of cardiac glycosides including oleandrin is needed.

Erdemoglu et al. (*J. Ethnopharmacol.* (2003) November 89(1), 123-129) discloses results for the comparison of aqueous and ethanolic extracts of plants, including *Nerium oleander*, based upon their anti-nociceptive and anti-inflammatory activities. Fartyal et al. (J. Sci. Innov. Res. (2014), 3(4), 426-432) discloses results for the comparison of methanol, aqueous, and petroleum ether extracts of *Nerium oleander* based upon their antibacterial activity.

Organic solvent extracts of *Nerium oleander* are also disclosed by Adome et al. (*Afr. Health Sci.* (2003) August 3(2), 77-86; ethanolic extract), el-Shazly et al. (*J. Egypt Soc. Parasitol*. (1996), August 26(2), 461-473; ethanolic extract), Begum et al. (*Phytochemistry* (1999) February 50(3), 435-438; methanolic extract), Zia et al. (*J. Ethnolpharmacol*. (1995) November 49(1), 33-39; methanolic extract), and Vlasenko et al. (*Farmatsiia*. (1972) September-October 21(5), 46-47; alcoholic extract). Turkmen et al. (*J. Planar Chroma*. (2013), 26(3), 279-283) discloses an aqueous ethanol extract of *Nerium oleander* leaves and stems. U.S. Pat. No. 3,833,472 issued Sep. 3, 1974 to Yamauchi discloses extraction of *Nerium odorum* SOL (*Nerium oleander* Linn) leaves with water, organic solvent, or aqueous organic solvent, wherein the leaves are heated to 60°-170° C. and then extracted, and the organic solvent is methanol, ethanol, propyl ether or chloroform.

A supercritical fluid (SCF) extract of *Nerium* species is known (PBI-05204; as described herein and in U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference). The SCF extract has demonstrated efficacy in treating some neurological disorders (U.S. Pat. Nos. 8,481,086, 9,220,778, 9,358,293, US 20160243143A1, U.S. Pat. No. 9,877,979, U.S. Ser. No. 10/383,886), some cell-proliferative disorders (U.S. Pat. Nos. 8,367,363, 9,494,589, 9,846,156), and some viral infections (U.S. Ser. No. 10/596,186, WO 2018053123A1, WO2019055119A1). Addington et al. (U.S. Pat. Nos. 8,481, 086, 9,220,778, 9,358,293, US 20160243143 A1) disclose use of PBI-05204 for the treatment of neurological conditions. Addington et al. (U.S. Pat. No. 9,011,937, US 20150283191 A1) disclose use of a triterpene-containing fraction (PBI-04711) for the treatment of neurological conditions. PBI-05204 comprises cardiac glycoside (oleandrin, OL) and triterpenes (oleanolic acid (OA), ursolic acid (UA) and betulinic acid (BA)) as the primary pharmacologically active components. The molar ratio of OA:UA:BA in PBI-05204 is about 7.8:7.4:1. PBI-04711 is a fraction of PBI-05204, but it does not contain OL. The molar ratio of OA:UA:BA in PBI-04711 is about 3:2.2:1.

Oleandrin may also be obtained from extracts of suspension cultures derived from *Agrobacterium tumefaciens*-transformed calli and from extracts of *agrobacterium* (Ibrahim et al., "Stimulation of oleandrin production by combined *Agrobacterium tumefaciens* mediated transformation and fungal elicitation in *Nerium oleander* cell cultures", in *Enz. Microb. Technol.* (2007), 41, 331-336).

Oleandrin may also be obtained from extracts of *Nerium oleander* microculture in vitro, whereby shoot cultures can be initiated from seedlings and/or from shoot apices of the *Nerium oleander* cultivars, e.g. *Splendens Giganteum*, Revanche or Alsace, or other cultivars (Vila et al., "Micropropagation of Oleander (*Nerium oleander* L.)" in *HortScience* (2010), 45(1), 98-102).

Extracts of *Nerium* species are known to contain many different classes of compounds: cardiac glycosides, glycones, aglycones, steroids, triterpenes, polysaccharides, saccharides, alkaloids, fat, proteins, and others. Specific compounds include oleandrin, neritaloside, odoroside, oleanolic acid, ursolic acid, betulinic acid, oleandrigenin, oleaside A, betulin (urs-12-ene-3☐,28-diol), 28-norurs-12-en-3☐-ol, urs-12-en-3☐-ol, 3☐,3☐-hydroxy-12-oleanen-28-oic acid, 3☐,20☐-dihydroxyurs-21-en-28-oic acid, 3☐,27-dihydroxy-12-ursen-28-oic acid, 3☐,13☐-dihydroxyurs-11-en-28-oic acid, 3☐,12☐-dihydroxyoleanan-28,13☐-olide, 3☐,27-dihydroxy-12-oleanan-28-oic acid, homopolygalacturonan, arabinogalaturonan, chlorogenic acid, caffeic acid, L-quinic acid, 4-coumaroyl-CoA, 3-O-caffeoylquinic acid, 5-O-caffeoylquinic acid, cardenolide B-1, cardenolide B-2, oleagenin, neridiginoside, nerizoside, odoroside-H, 3-beta-O-(D-diginosyl)-5-beta, 14 beta-dihydroxy-card-20(22)-enolide pectic polysaccharide composed of galacturonic acid, rhamnose, arabinose, xylose, and galactose, polysaccharide with MW in the range of 17000-120000 D, or MW about 35000 D, about 3000 D, about 5500 D, or about 12000 D, cardenolide monoglycoside, cardenolide N-1, cardenolide N-2, cardenolide N-3, cardenolide N-4, pregnane, 4,6-diene-3,12,20-trione, 20R-hydroxypregna-4,6-diene-3,12-dione, 16beta,17beta-epoxy-12beta-hydroxypregna-4,6-diene-3,20-dione, 12beta-hydroxypregna-4,6,16-triene-3, 20-dione (neridienone A), 20S,21-dihydroxypregna-4,6-diene-3,12-dione (neridienone B), neriucoumaric acid, isoneriucoumaric acid, oleanderoic acid, oleanderen, 8alpha-methoxylabdan-18-oic acid, 12-ursene, kaneroside, neriumoside, 3β-O-(D-diginosyl)-2α-hydroxy-8,14β-epoxy-5β-carda-16:17, 20:22-dienolide, 3β-O-(D-diginosyl)-2α,14β-dihydroxy-5β-carda-16:17,20:22-dienolide, 3β,27-dihydroxy-urs-18-en-13,28-olide, 3β,22α,28-trihydroxy-25-nor-lup-1(10),20(29)-dien-2-one, cis-karenin (3β-hydroxy-28-Z-p-coumaroyloxy-urs-12-en-27-oic acid), trans-karenin (3-β-hydroxy-28-E-p-coumaroyloxy-urs-12-en-27-oic acid), 3beta-hydroxy-5alpha-carda-14(15),20 (22)-dienolide (beta-anhydroepidigitoxigenin), 3 beta-O-(D-digitalosyl)-21-hydroxy-5beta-carda-8,14,16,20(22)-tetraenolide (neriumogenin-A-3beta-D-digitaloside), proceragenin, neridienone A, 3beta,27-dihydroxy-12-ursen-28-oic acid, 3beta,13beta-dihydroxyurs-11-en-28-oic acid, 3beta-hydroxyurs-12-en-28-aldehyde, 28-orurs-12-en-3beta-ol, urs-12-en-3beta-ol, urs-12-ene-3beta,28-diol, 3beta,27-dihydroxy-12-oleanen-28-oic acid, (20S, 24R)-epoxydammarane-3beta,25-diol, 20beta,28-epoxy-28alpha-methoxytaraxasteran-3beta-ol, 20beta,28-epoxytaraxaster-21-en-3beta-ol, 28-nor-urs-12-ene-3beta,17 beta-diol, 3beta-hydroxyurs-12-en-28-aldehyde, alpha-neriursate, beta-neriursate, 3alpha-acetophenoxy-urs-12-en-28-oic acid, 3beta-acetophenoxy-urs-12-en-28-oic acid, oleanderolic acid, kanerodione, 3β-p-hydroxyphenoxy-11α-methoxy-12α-hydroxy-20-ursen-28-oic acid, 28-hydroxy-20(29)-lupen-3,7-dione, kanerocin, 3alpha-hydroxy-urs-18, 20-dien-28-oic acid, D-sarmentose, D-diginose, neridiginoside, nerizoside, isoricinoleic acid, gentiobiosylnerigoside, gentiobiosylbeaumontoside, gentiobiosyloleandrin, folinerin, 12β-hydroxy-5β-carda-8,14,16,20(22)-tetraenolide, 8β-hydroxy-digitoxigenin, Δ16-8β-hydroxy-digitoxigenin, Δ16-neriagenin, uvaol, ursolic aldehyde, 27(p-coumaroyloxy)ursolic acid, oleanderol, 16-anhydro-deacteyl-nerigoside, 9-D-hydroxy-cis-12-octadecanoic acid, adigoside, adynerin, alpha-amyrin, beta-sitosterol, campestrol, caoutchouc, capric acid, caprylic acid, choline, cornerin, cortenerin, deacetyloleandrin, diacetyl-nerigoside, foliandrin, pseudocuramine, quercetin, quercetin-3-rhamnoglucoside, quercitrin, rosaginin, rutin, stearic acid, stigmasterol, strospeside, urehitoxin, and uzarigenin. Additional components that may be present in the extract are disclosed by Gupta et al. (IJPSR (2010(, 1(3), 21-27, the entire disclosure of which is hereby incorporated by reference).

The respective compositional profile of said extracts varies widely according to the method of extraction employed. For example, extracts of *Nerium* plant material obtained using hot methanol, hot ethanol, hot water, cold water, hot water, or supercritical carbon dioxide exhibit substantially different compositional profiles, especially as indicated by respective HPLC chromatograms. Accordingly, one cannot predict a priori the compositional profile of an extract prepared by a new type of process.

The therapeutic activity profile of such extracts will also vary according to the compositional profile of the extract, when compared on a total weight to total weight basis. For example, 1 mg of cold-water extract will exhibit a different therapeutic activity profile than 1 mg of supercritical fluid extract. Moreover, the SCF extract has demonstrated improved efficacy over oleandrin alone and even over the hot-water extract in treating some conditions.

Given the important therapeutic properties of oleandrin and extracts containing oleandrin and other components of the *Nerium* plant, a need remains for improved pharmaceutical compositions containing oleandrin and for improved methods of producing oleandrin and oleandrin-containing extracts.

SUMMARY OF THE INVENTION

The present invention seeks to overcome some or all of the disadvantages inherent in the art. Objects of the invention include providing an improved process for production of oleandrin-containing extract, and an improved process for production of oleandrin. Another object of the invention includes providing an oleandrin-containing extract and an oleandrin-containing composition. Another object of the invention provides a sublingual or buccal dosage form comprising the extract (or composition) and at least one pharmaceutical excipient. Another object of the invention is to provide pharmaceutical compositions, dosage forms, cosmetics, and nutraceutical products containing oleandrin or the extract(s) described herein.

The improved process(es) provide(s) a) a higher yield of oleandrin per kg of plant biomass as compared to a supercritical fluid (SCF) extraction (SCFE)-based process; b) an oleandrin-containing composition with a higher ratio of oleandrin to other components as compared to a SCFE process; c) a dual extract composition comprising an organic solvent extract and a subcritical extract; d) an organic solvent extract with a higher content of oleandrin as compared to a SCFE process obtained from the same amount of plant material; e) a subcritical $CO_2$ extract with a higher content of oleandrin as compared to a SCF extract obtained using the same solvent(s) and same amount of plant material.

In each embodiment of the organic solvent extract or organic solvent extraction, the organic solvent comprises a) one or more organic solvents; or b) water and one or more organic solvent extracts. The water may further comprise one or more salts, one or more buffers, or a combination thereof.

An aspect of the invention provides a method of producing oleandrin-containing extract, the method comprising
- subjecting oleandrin-containing biomass to subcritical liquid extraction (SbCLE) employing subcritical liquid (SbCL) comprising carbon dioxide, optionally further comprising organic solvent (modifier), for a period of time sufficient to extract the oleandrin and form extraction milieu;
- separating said biomass from said extraction milieu to provide oleandrin-containing SbCL; and
- removing SbCL from said oleandrin-containing SbCL to provide said oleandrin-containing (OC) extract (OCE).

An aspect of the invention provides a method of producing oleandrin, the method comprising
- subjecting oleandrin-containing biomass to subcritical liquid extraction (SbCLE) employing subcritical liquid (SbCL) comprising carbon dioxide, optionally further comprising organic solvent (modifier), for a period of time sufficient to extract the oleandrin to form extraction milieu;
- separating said biomass from said extraction milieu to provide oleandrin-containing SbCL;
- removing SbCL from said oleandrin-containing SbCL to provide oleandrin-containing extract; and
- isolating oleandrin from said extract.

Another aspect of the invention provides a method of producing a combination composition, the method comprising
- subjecting oleandrin-containing first biomass to organic solvent extraction to provide an oleandrin-containing organic solvent extract;
- subjecting oleandrin-containing second biomass to subcritical liquid (SbCL) extraction (SbCLE) to provide an oleandrin-containing SbCL extract; and
- combining said oleandrin-containing organic solvent extract and said oleandrin-containing SbCL extract to provide said combination composition.

In some embodiments, the combination composition comprises at least oleandrin, oleanolic acid, ursolic acid, betulinic acid, kanerocin, kanerodione, oleandrigenin, *Nerium* F, neritaloside, odoroside (A and H), adynerin, odoroside-G-acetate, and gitoxigenin. The combination composition may further comprise one or more of neriin, folinerin, gitoxigenin, digitoxigenin, nerigoside, rutin, ursonic acid, neridienone A, adynerigenin, deacetyloleandrin, odoroside G acetate, and/or quercetin.

The composition (or the extract) may further comprise polyphenol(s), carbohydrate(s), flavonoid(s), amino acid(s), soluble protein(s), cellulose, starch, alkaloid(s), saponin(s), tannin(s), and any combination thereof.

The amino acid can be selected from the group consisting of aspartic acid, glutamic acid, asparagine, serine, glutamine, glycine, histidine, arginine, threonine, alanine, proline, tyrosine, valine, methionine, cysteine, isoleucine, leucine, phenylalanine, tryptophan, and lysine. In some embodiments, the amino is selected from the group consisting of asparagine, arginine, threonine, alanine, proline, tyrosine, valine, isoleucine, leucine, phenylalanine, tryptophan, and lysine.

Another aspect of the invention provides a cosmetic (cosmeceutical) product or a nutraceutical product comprising oleandrin, oleandrin-containing composition, oleandrin-containing combination composition, or oleandrin-containing extract(s) as defined herein.

The cosmetic product may further comprise one or more cosmetic excipients. The cosmetic product can be a cleanse, shampoo, conditioner, body wash, face cleanser, skin toner, serum, moisturizer, balm, makeup, lotion, cream, gel, hydrogel, ointment, oil-based solution, suspension, powder, spray, foundation, primer, highlighter, eye shadow, foundation, blush, towelette, deodorant, bath oil, bubble bath, bath salt, body butter, lipstick, lip gloss, lip liner, concealer, rouge, facial mask treatment, or any other type of cosmetic product.

A nutraceutical can include a dietary ingredient, dietary supplement, bioceutical, or food additive such as may be defined by the USFDA or other regulatory agencies. The nutraceutical product may further comprise one or more nutraceutical or dietary ingredients. The nutraceutical may include a liquid, solid, powder, cream, solution, suspension, dosage form, gel, capsule, tablet, pill, prebiotic, probiotic, functional food, meal supplement, meal replacement, or other such products.

The invention also provides an improved oleandrin-containing combination composition comprising a portion of oleandrin-containing organic solvent extract and a portion of oleandrin-containing SbCL extract. In some embodiments, a) substantially equal portions of the two extracts are present in the combination composition; b) the content of organic solvent extract in said combination is higher than the content of SbCL extract; or c) the content of SbCL extract in said combination is higher than the content of organic solvent extract. Respective methods of preparation and methods of use are also provided substantially as described herein.

As compared to either the organic solvent extract and the subcritical liquid extract, the combination composition advantageously comprises a greater range of phytochemicals and other components, aside from oleandrin, extractable from the plant material. It is known that one or more of those other components are also therapeutically effective (pharmacologically active) ingredients.

Embodiments of the invention include those wherein a) the organic solvent extract comprises at least oleandrin and other components extracted from the biomass; b) in the organic solvent extract, the molar ratio of oleandrin to other components extracted from the biomass is greater than said molar ratio in the subcritical liquid extract; c) the SbCL extract comprises at least oleandrin and other components extracted from the biomass; d) the content of oleandrin in the ethanolic extract is greater than the content of oleandrin in the subcritical liquid extract; e) the content of extracted non-oleandrin components in the organic solvent extract is greater than the content of said components in said subcritical liquid extract; f) the compositional profile of extracted volatile and semi-volatile components in said organic solvent extract is different than the compositional profile of said components in said subcritical liquid extract; and/or g) relative to oleandrin content, the subcritical liquid extract comprises a greater proportion of extracted volatile and semi-volatile components than does the organic solvent extract.

The first and second biomass may be the same or different. The first biomass extracted with organic solvent may be used as the second biomass; alternatively, the first biomass is extracted with organic solvent, and a different second biomass is extracted with subcritical liquid.

Embodiments of the invention include those wherein the subcritical liquid extraction process further comprises one or more of the following: a) separating said biomass from the extraction milieu by filtering the extraction milieu; b) adding modifier to the carbon dioxide or extraction milieu; c) heating and pressurizing the interior of a vessel containing the extraction milieu to form subcritical liquid phase extraction milieu; d) removing said SbCL from said oleandrin-containing SbCL by volatilizing said SbCL to form raw SbCL extract (SbCLE); e) diluting the raw SbCL extract with organic solvent or aqueous organic solvent; f) filtering the diluted raw or crude SbCL extract one or more times; g) treating the diluted raw or crude SbCL extract with activated carbon; h) removing most of the organic solvent from the diluted raw extract to form; and/or i) sterile filtering the raw or crude extract to obtain the SbCL extract. The SbCL extract is optionally further diluted with organic solvent or aqueous organic solvent. The organic solvent extract is optionally further diluted with organic solvent or aqueous organic solvent. The SbCL extract may comprise 0.1 mg to 1 mg or 0.5 to 0.8 mg of oleadrin per mL of extract.

Embodiments of the invention include those wherein the carbon dioxide (along with any modifier, if any is present) is in the subcritical liquid phase during about 50% or more of the extraction time period, i.e. about 50% or more of the total time for the "subjecting" step. In some embodiments, the extraction milieu, comprising extraction fluid (carbon dioxide along with any modifier, if any is present) in the subcritical liquid phase and biomass, will remain in liquid form for at least 60%, at least 70%, at least 80%, at least 90%, at least 95%, or at least 99% of the extraction period. In some embodiments, the extraction milieu will remain in liquid form throughout the extraction period.

Accordingly, the SbCLE is conducted such that the extraction milieu (comprising biomass and $CO_2$, and optionally further comprising organic solvent (modifier)) is under the following conditions, with respect to the phase diagram of $CO_2$, during about 50% or more of the extraction time period: a) at or below the critical pressure ($p_c$), at or above the triple point (solid-liquid-gas) temperature ($t_{tp}$), below the critical temperature ($t_c$), and above the liquid-gas phase line; b) at or below the $t_c$, at or above the $t_{tp}$, below the $p_c$, and above the liquid-gas phase line; c) at or above the $p_c$, below the $t_c$, at or above the $t_{tp}$, above the liquid-gas phase line, and below the solid-liquid phase line; or d) at a temperature and pressure falling within the liquid region bounded by the solid-liquid phase line, the liquid-gas phase line, the liquid-supercritical phase line, the $t_{tp}$, the triple point pressure ($p_{tp}$), the critical point (liquid-gas-supercritical) temperature ($t_{cp}$), and the critical point pressure ($p_{cp}$). The critical pressure and temperature are with respect to $CO_2$.

Embodiments of the invention include those wherein SbCLE is conducted at a temperature of about 0° C. up to about 31° C. and a pressure of about 5.2 bar to about 3000 bar. Other embodiments of the invention include those wherein SbCLE is conducted at a temperature of about 0° C. up to about 31° C. and a pressure of about 5.2 bar to about 1000 bar. In preferred embodiments, SbCLE is conducted at a temperature of about 2° C. to about 16° C. and a pressure of about 115 bar to about 135 bar. In other preferred embodiments, SbCLE is conducted at a temperature of about 5-10° C. and a pressure of about 120-130 bar. In some embodiments, the SbCLE is conducted at a temperature in the range of about 5° C. to about 15° C. and a pressure in the range of about 50 bar to 70 bar.

Embodiments of the invention include those wherein the SbCL further comprises one or more modifiers, e.g. organic solvent(s). When the one or more modifiers is(are) present, the weight ratio of carbon dioxide to modifier is about 100:about 0.01-20, about 100:about 0.01-15, about 100: about 0.01-10, or about 100:about 0.01-5.

The one or more modifiers (organic solvents) may be independently selected upon each occurrence from alcohol, organic solvent, alkyl ketone, alkyl ester, water. Particularly suitable modifiers include ethanol, methanol propanol, acetone, ethyl acetate, methyl ethyl ketone, glycol (e.g. propylene glycol), dimethyl sulfoxide (DMSO), N,N-dimethylformamide (DMF), or N-methylpyrrolidone (NMP)

Embodiments of the invention include those wherein a) said organic solvent extraction is conducted with organic solvent or aqueous organic solvent; b) independently upon each occurrence, said organic solvent or aqueous organic solvent comprises alcohol; c) independently upon each occurrence, said organic solvent is selected from the group consisting of methanol, ethanol, propanol, butanol, chloroform, methylene chloride, ethyl acetate, and a combination thereof; d) said organic solvent extraction comprises extracting said oleandrin-containing biomass with organic solvent or aqueous organic solvent one or more times; e) independently upon each occurrence, said aqueous organic solvent comprises up to about 20% w/w, about 5% w/w to about 15% w/w, or about 10% w/w of water; f) said organic solvent extract is conducted at a temperature of from about 0° C. to about 75° C., about 5° C. to about 70° C., about 10° C. to about 60° C., about 10° C. to about 50° C., about 10° C. to about 45° C., or about 20° C. to about 40° C.; g) the v/w ratio of organic solvent (or aqueous organic solvent) to biomass is in the range of about 50-1:about 1, about 40-1: about 1, about 30-1:about 1, about 20-1:about 1, about 20-5:about 1, or about 10:about 1. Where undessicated or undehydrated or unfreeze-dried biomass is used for extraction, the water content included in the biomass is accounted for as the v/w ratio of aqueous organic solvent to biomass (dry weight basis).

Embodiments of the invention include those wherein the organic solvent extraction further comprises one or more of the following: a) separating said biomass from the extraction milieu by filtering the extraction milieu to form crude extract; b) adding aqueous liquid to the organic solvent or extraction milieu; c) reducing the content of organic solvent from said crude extract; d) treating the crude extract with activated carbon; e) filtering the crude extract one or more times; f) adding additional organic solvent to the crude extract; g) sterile filtering the organic solvent extract; and/or h) adding water to the crude extract and extracting the aqueous crude extract with organic solvent. The organic solvent extract is optionally further diluted with organic solvent or aqueous organic solvent. The organic solvent extract may comprise 0.1 to 10 mg/mL, 0.5 to 8 mg/mL, 1 to 8 mg/mL, 1.5 to 8 mg/mL, or 1.5 to 5 mg/mL (mg of oleandrin per mL of extract).

Embodiments of the invention include those wherein the oleandrin-containing biomass is *Nerium* sp., *Nerium oleander*, *Nerium oleander* L (Apocynaceae), *Nerium odourum*, *Nerium indicum*, white oleander, pink oleander, *Thevetia* sp., *Thevetia peruviana*, yellow oleander, *Agrobacterium tumefaciens*, or a combination thereof. In some embodiments, the biomass comprises leaves, stems, flowers, bark, fruits, seeds, sap, cultured cellular mass, and/or pods.

Embodiments of the invention include those wherein a) independently upon each occurrence, the biomass is dehydrated, dehumidified, freeze-dried, and/or desiccated prior to extraction; b) independently upon each occurrence, the biomass is dried prior to extraction; c) independently upon each occurrence, the biomass is not dehydrated prior to extraction; d) independently upon each occurrence, the biomass is not dried prior to extraction; or e) independently upon each occurrence. The water content in the biomass is preferably about 20 wt % or less, about 15 wt % or less, about 10 wt % or less, about 8 wt % or less, about 5 wt % or less, about 2.5 wt % or less, or about 1 wt % of less, prior to extraction. Accordingly, the method of the invention also includes embodiments further comprising dehydrating, drying or desiccating the biomass prior to extraction.

Embodiments of the invention include those wherein a) prior to extraction, the biomass has an average particle size (d0.5) of less than about 1", less than about 0.75", less than about 0.5", less than about 0.4", less than about 0.3", less than about 0.2", less than about 0.1", less than about 0.05", or less than about 0.01", said particle being with respect to ASTM sieve mesh opening size.

Embodiments of the invention include those wherein a) the content of oleandrin in said extract is about 0.01 wt % or higher, about 0.05 wt % or higher, about 0.1 wt % or higher, about 0.2 wt % or higher, about 0.5 wt % or higher, about 1 wt % or higher, about 2.5 wt % or higher, about 5 wt % or higher, about 10 wt % or higher, about 20 wt % or higher, about 30 wt % or higher, about 40 wt % or higher, about 50 wt % or higher, about 60 wt % or higher, about 70 wt % or higher, about 80 wt % or higher, or about 90 wt % or higher; b) the content of oleandrin in said extract is about 99 wt % or lower, about 95 wt % or lower, about 90 wt % or lower, about 80 wt % or lower, about 70 wt % or lower, about 60 wt % or lower, about 50 wt % or lower, about 40 wt % or lower, about 30 wt % or lower, about 20 wt % or lower, about 10 wt % or lower, about 5 wt % or lower, about 2.5 wt % or lower, about 1 wt % or lower, or about 0.5 wt % or lower; or c) a combination of any limit of item a) and any limit of item b).

Embodiments of the invention include those wherein the process further comprises one or more of the following: a) removing (or reducing the amount of) volatile organic compounds (VOC's) from said extract; b) removing (or reducing the amount of) semi-volatile organic compounds (SVOC's) from said extract; c) filtering said extract; d) said separating is conducted by filtration, centrifugation, decantation, or a combination thereof.

Embodiments of the invention include those wherein said isolating is achieved by one or more of chromatography, liquid-liquid extraction, liquid-solid extraction, crystallization, precipitation, fractional precipitation, fractional crystallization, Soxhlet extraction, trituration, lyophilization (freeze-drying), or a combination thereof.

The individual steps of any of the methods of the invention can be conducted at separate facilities or within the same facility.

Pharmaceutical compositions comprising oleandrin as the sole active ingredient are within the scope of the invention. Compositions comprising oleandrin and plural active ingredients obtained from said biomass are within the scope of the invention. Compositions comprising oleandrin and plural triterpenes as the active ingredients are within the scope of the invention. In some embodiments, said composition comprises oleandrin, oleanolic acid (free acid, salt, derivative or prodrug thereof), ursolic acid (free acid, salt, derivative or prodrug thereof), and betulinic acid (free acid, salt, derivative or prodrug thereof). The molar ratios of the compounds are as described herein. A triterpene is independently selected upon each occurrence from its free acid form, salt form, deuterated form and derivative form.

In addition to oleandrin, the extract may comprise one or more other compounds (which may or may not be pharmacologically active, therapeutically effective) extracted from the biomass during the extraction process. The one or more other compounds may or may not contribute to the therapeutic efficacy of oleandrin when administered to a subject receiving both. The one or more other compounds can be selected from the group consisting of cardiac glycoside, one or more glycone constituents of cardiac glycosides (such as glucoside, fructoside, and/or glucuronide), one or more aglycones, one or more glycoside precursors (such as cardenolides, cardadienolides and cardatrienolides), one or more steroids, one or more triterpenes, one or more saccharides, one or more polysaccharides, one or more alkaloids, one or more proteins, fat, one or more other non-cardiac glycoside therapeutically effective agent, and any combination thereof. In some embodiments, the composition comprises oleandrin and: a) two or three triterpenes; b) two or three triterpene derivatives; c) two or three triterpene salts; or d) a combination thereof. As used herein, the generic terms triterpene and cardiac glycoside also encompass free form, salt form and derivatives thereof, unless otherwise specified. In some embodiments, the triterpene is selected from the group consisting of oleanolic acid, ursolic acid, betulinic acid and salts or derivatives thereof.

In some embodiments, the organic extract comprises oleandrin and a) one or more volatile organic compounds; b) one or more semi-volatile organic compounds; c) one or more nonvolatile organic compounds; or d) any combination thereof.

In some embodiments, the extract excludes a pharmacologically active polysaccharide (and/or saccharide) obtained during extraction. In some embodiments, the extract comprises oleandrin and at least one pharmacologically active polysaccharide (and/or saccharide) obtained during extraction. The pharmacologically active polysaccharide may be an acidic homopolygalacturonan or arabinogalaturonan.

In some embodiments, the extract comprises at least oleandrin, oleanolic acid, ursolic acid, betulinic acid, kanerocin, kanerodione, oleandrigenin, *Nerium* F, neritaloside, odoroside (A and H), adynerin, odoroside-G-acetate, and gitoxigenin. The combination composition may further comprise one or more of neriin, folinerin, gitoxigenin, digitoxigenin, nerigoside, rutin, ursonic acid, neridienone A, adynerigenin, deacetyloleandrin, odoroside G acetate, and/or quercetin.

The extract may further comprise one or more polyphenol(s), one or more carbohydrate(s), one or more flavonoid(s), one or more amino acid(s), one or more soluble protein(s), one or more cellulose(s), one or more starch(es), one or more alkaloid(s), one or more saponin(s), one or more tannin(s), and any combination thereof.

The amino acid can be selected from the group consisting of aspartic acid, glutamic acid, asparagine, serine, glutamine, glycine, histidine, arginine, threonine, alanine, proline, tyrosine, valine, methionine, cysteine, isoleucine, leucine, phenylalanine, tryptophan, and lysine. In some embodiments, the amino is selected from the group consisting of asparagine, arginine, threonine, alanine, proline, tyrosine, valine, isoleucine, leucine, phenylalanine, tryptophan, and lysine.

It should be understood that even though other components in the extract may be present in greater relative quantity than oleandrin, oleandrin may be the primary therapeutically effective compound with respect specific diseases, disorders or conditions.

Some embodiments of the invention include those wherein a pharmaceutical composition comprises at least one pharmaceutical excipient and the extract.

The oleandrin, oleandrin-containing extract, or oleandrin-containing composition of the invention can be administered to a subject in need thereof to treat a condition, disease or disorder that is therapeutically responsive to treatment with cardiac glycoside (oleandrin, digoxin, digitoxin, ouabain, bufalin, cinobufatalin, cinobufagin, resibufogenin, lanatoside C, or other therapeutically effective cardiac glycoside), in particular to treatment with oleandrin, or which can be prevented by administration of cardiac glycoside, in particular administration of oleandrin.

An aspect of the invention provides a method of treating or preventing a condition, disease or disorder that is therapeutically responsive to oleandrin (oleandrin-containing composition or oleandrin-containing extract), the method comprising administering to a subject in need thereof one or more doses of oleandrin (oleandrin-containing composition or oleandrin-containing extract), thereby treating or preventing said condition, disease or disorder. Target conditions, diseases and disorders are described herein.

Another aspect of the invention provides a method of improving or boosting the immunological response of a subject, the method comprising administering to a subject in need thereof one or more doses of oleandrin (oleandrin-containing composition, oleandrin-containing combination composition, or oleandrin-containing extract) in an amount sufficient to boost the subject's immunological response. The one or more doses can be administered as a pharmaceutical composition, nutraceutical composition, and/or cosmeceutical composition.

Administration can be acute, chronic, or a combination thereof and can occur before and/or after initiation of said condition, disease or disorder. Administration can be to a subject that has or is at risk of getting said condition, disease or disorder.

The oleandrin, oleandrin-containing extract, oleandrin-containing composition, or oleandrin-containing combination composition of the invention can be included in any pharmaceutical composition, nutraceutical composition, cosmeceutical compositions, or dosage form as described herein.

The oleandrin, oleandrin-containing extract, or oleandrin-containing composition of the invention can be administered locally, systemically or a combination thereof. Suitable modes of administration are described herein.

In some embodiments, oleandrin is present as the primary therapeutic component, meaning the component primarily responsible for therapeutic activity, in a pharmaceutical composition.

The invention also provides use of oleandrin-containing extract in the manufacture of a medicament for the treatment, in a subject, of a condition, disease or disorder that is therapeutically responsive to cardiac glycoside. In some embodiments, the manufacture of such a medicament comprises: providing oleandrin-containing extract; including a dose of oleandrin-containing extract in a pharmaceutical dosage form; and packaging the pharmaceutical dosage form. In some embodiments, the manufacture can be conducted as described in PCT International Application No. PCT/US06/29061, the entire disclosure of which is hereby incorporated by reference. The manufacture can also include one or more additional steps such as: delivering the packaged dosage form to a vendor (retailer, wholesaler and/or distributor); selling or otherwise providing the packaged dosage form to a subject having a viral infection; including with the medicament a label and a package insert, which provides instructions on use, dosing regimen, administration, content and toxicology profile of the dosage form.

In some embodiments, the treatment comprises: determining that a subject has a condition, disease or disorder that is therapeutically responsive to cardiac glycoside, e.g. oleandrin (oleandrin-containing composition or oleandrin-containing extract), digoxin, ouabain, bufalin, cinobufatalin, cinobufagin, resibufogenin, or other therapeutically effective cardiac glycoside; indicating administration of pharmaceutical dosage form to the subject according to a dosing regimen; administering to the subject one or more pharmaceutical dosage forms, wherein the one or more pharmaceutical dosage forms is administered according to the dosing regimen.

The pharmaceutical composition can further comprise a combination of at least one material selected from the group consisting of a water soluble (miscible) co-solvent, a water insoluble (immiscible) co-solvent, a surfactant, an antioxidant, a chelating agent, and an absorption enhancer.

The solubilizer is at least a single surfactant, but it can also be a combination of materials such as a combination of: a) surfactant and water miscible solvent; b) surfactant and water immiscible solvent; c) surfactant, antioxidant; d) surfactant, antioxidant, and water miscible solvent; e) surfactant, antioxidant, and water immiscible solvent; f) surfactant, water miscible solvent, and water immiscible solvent; or g) surfactant, antioxidant, water miscible solvent, and water immiscible solvent.

The composition(s) of the invention optionally further comprises a) at least one liquid carrier; b) at least one emulsifying agent; c) at least one solubilizing agent; d) at least one dispersing agent; e) at least one other excipient; or f) a combination thereof.

In some embodiments, the water miscible solvent is low molecular weight (less than 6000) PEG, glycol, or alcohol. In some embodiments, the surfactant is a pegylated surfactant, meaning a surfactant comprising a poly(ethylene glycol) functional group.

The invention also provides a buccal or sublingual dosage form comprising any extract(s) of the invention as described herein, and at least one pharmaceutical excipient. Said dosage form is adapted to deliver components of the extract to the mucosa of the mouth. Suitable dosage forms include tablet, wafer, patch, spray, drop, liquid, solution, paste, gel, film, bioadhesive composition, gummy, or powder.

The combination composition can be included in any type of pharmaceutical dosage form. Suitable ones are selected from the group consisting of solid dosage form, liquid dosage form, parenteral dosage form, otic dosage form, ophthalmic dosage form, nasal dosage form, inhalable dosage form, buccal dosage form, sublingual dosage form, enteral dosage form, topical dosage form, oral dosage form, peroral dosage form, injectable dosage form, tablet, capsule, pill, caplet, troche, sache, solution, suspension, dispersion, vial, bag, bottle, injectable liquid, i.v. (intravenous), i.m. (intramuscular) or i.p. (intraperitoneal) administrable liquid.

The dosage form can be a rapid release, immediate release, controlled release, sustained release, prolonged release, extended release, burst release, continuous release, slow release, or pulsed release dosage form, or is a dosage form that exhibits two or more of those types of release. When placed in an aqueous environment or after administration to a subject, the dosage form may exhibit a drug release profile selected from the group consisting of zero order, pseudo-zero, first order, pseudo-first order or sigmoidal release profile.

In some embodiments, the dosage form a) releases its charge of composition within a period of 0.5 to 1 hours or less; b) is enteric coated and releases its charge of composition downstream of the stomach, such as in the jejunum, ileum, small intestine, and/or large intestine; or c) is enteric coated and releases its charge of composition into the systemic circulation within 1-10 hr after oral administration In some embodiments, the inhalable, buccal or sublingual dosage form further comprises at least one bitter taste antagonist (also referred to as a bitter receptor blocker). The bitter taste antagonist inhibits the taste receptor activation caused by a bitter compound, such as a cardiac glycoside. In preferred embodiments, the bitter taste antagonist inhibits activation of at least one of the receptors of the hTAS2R family of G protein-coupled receptors. As used herein, the bitter taste antagonist can include taste-masking agent(s). Suitable bitter taste antagonists include GIV3757 (4-(2,2,3-trimethylcyclopentyl)butanoic acid), gamma-aminobutyric acid (GABA), 6-methoxy-flavanone, 4'-fluoro-6-methoxyflavanone, 6,3'-dimethoxyflavanone, 6-methoxyflavanone, abscisic acid, (−)-hardwickiic acid (2-(fitran-3-yl)ethyl)-trimethyl-hexahydronaphthalene-carboxylic acid), fenchone, borneol, isoborneol, anethole, menthofuran, monosodium glycyrrhizinate, pullulan (α-1,4-; α-1,6-glucan), flavorant, or sweetener. Suitable flavorant(s) include mint, peppermint, menthol, eucalyptus, eucalyptol, chocolate, spearmint, tangerine, orange, grape, grapefruit, marshmallow, coffee, banana crème, caramel, bubble gum, cherry, lemon, lime, strawberry, maple, raspberry, and/or apple. Suitable sweetener(s) include magnasweet (110 or 135), sucralose, steviol glycoside(s), stevia, glycerin, acesulfame potassium, PCCA sweetness enhnancer, PCCA bitter stop, di-d-fructofuranose 1,2': 2,3'-di-anhydride, aspartame, neohesperidine dihydrochalcone and hesperidine dihydrochalcone 4'-β-d glucoside, d-sorbitol, sodium saccharin, sodium gluconate, and/or monosodium glutamate. The inhalable, buccal or sublingual dosage form can also include an oil-based excipient such as a fixed oil (e.g. from almond, peanut, sesame, olive, avocado, or corn), or hydrogenated oil. The inhalable, buccal or sublingual dosage form may also be taste-masked with taste masking by polymer coating; taste masking by conventional granulation; taste masking with ion-exchange resins; taste masking by spray congealing with lipids; taste masking by formation of inclusion complexes with cyclodextrins; taste masking by the freeze-drying process; taste masking by making multiple emulsions; and taste masking with gelatin, gelatinized starch, liposomes, lecithins or lecithin-like substances, surfactants, salts, or polymeric membranes.

In some embodiments, the inhalable, buccal or sublingual dosage form further comprises one or more permeation enhancers that improve mucosal permeability and absorption of compounds, such as cardiac glycoside(s). Suitable permeation enhancer(s) include surfactants, bile salts, fatty acids, cyclodextrins, and chelators.

The invention includes all combinations of the aspects, embodiments and sub-embodiments of the invention disclosed herein.

BRIEF DESCRIPTION OF THE FIGURES

The following figures form part of the present description. The skilled artisan will, in light of these figures and the description herein, be able to practice the invention without undue experimentation.

DETAILED DESCRIPTION OF THE INVENTION

Figure 1:
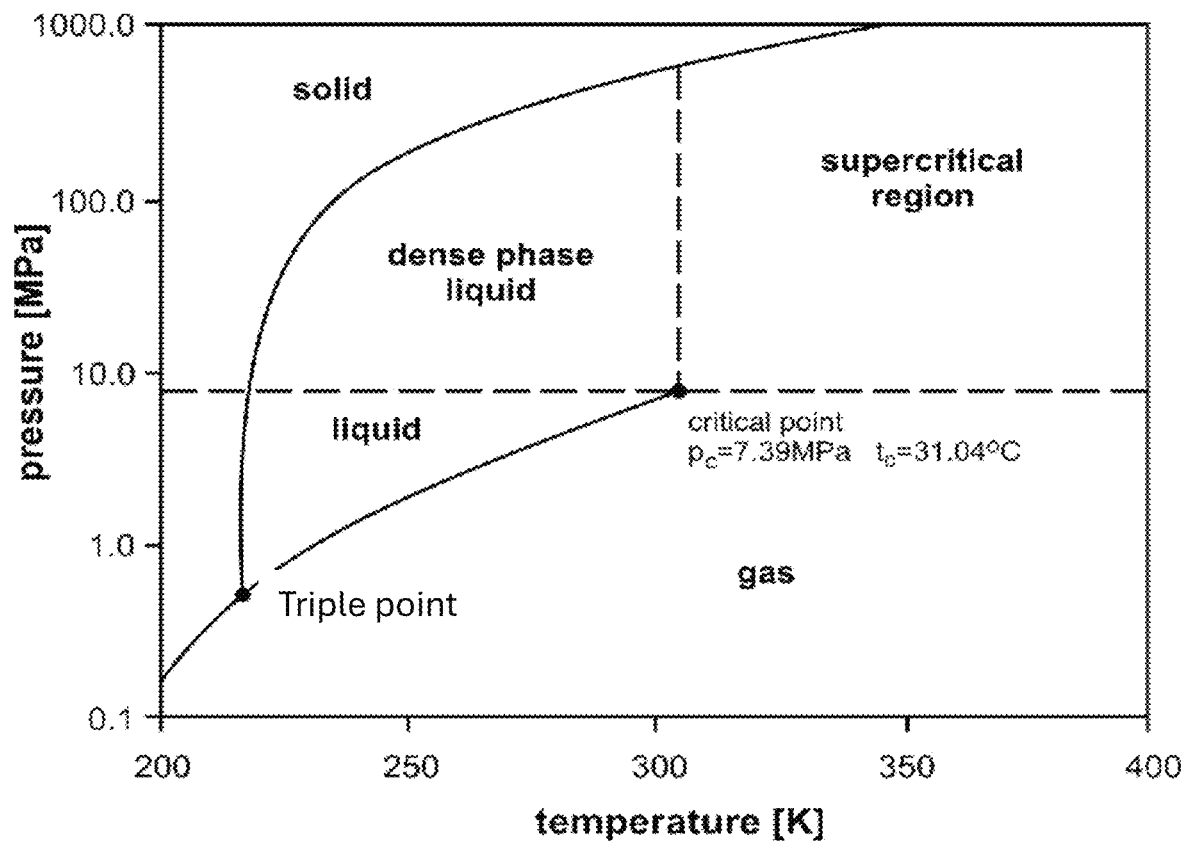
FIG. 1 depicts a phase diagram for carbon dioxide indicating the solid, liquid, gas and supercritical phases as well as the triple point and critical point temperatures and pressures. The solid and liquid phases are separated by the solid-liquid phase line. The liquid and gas phases are separated by the liquid-gas phase line. The supercritical fluid and liquid phases are separated by the supercritical fluid-liquid phase line. The liquid region is thus bounded by the liquid-gas phase line, solid-liquid phase line, supercritical fluid-liquid phase line, triple point (temperature and pressure) and critical point (temperature and pressure).
Figure 2:
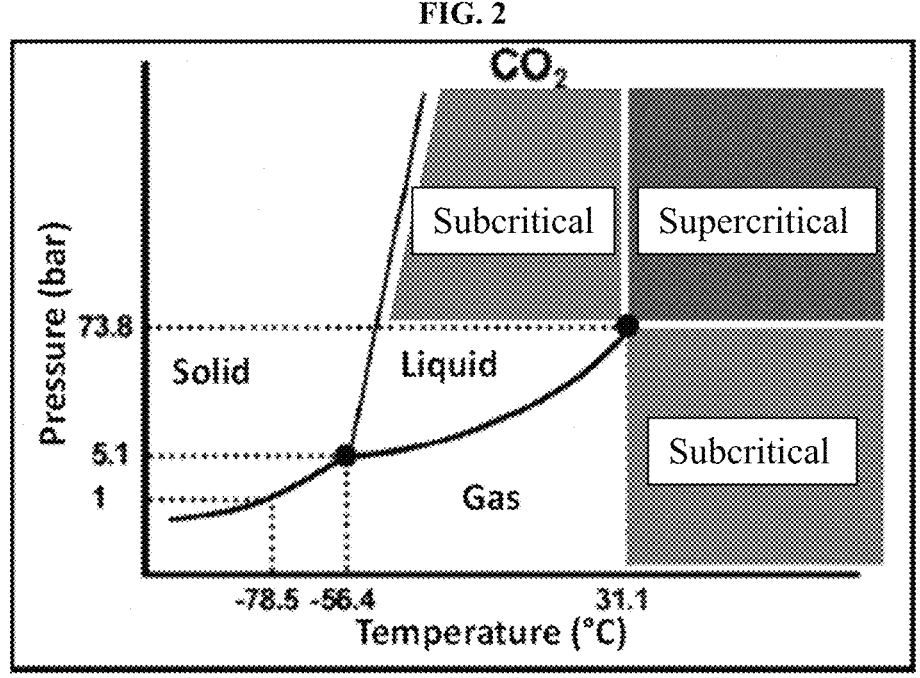
FIG. 2 depicts a phase diagram for carbon dioxide indicating the supercritical region and two of the subcritical regions: a subcritical liquid region and a subcritical gas region.

The invention provides an oleandrin-containing subcritical extract, an oleandrin-containing organic solvent extract, and a combination composition comprising said subcritical extract and said organic solvent extract. The invention also provides pharmaceutical compositions comprising at least one pharmaceutical excipient and said extract(s) or combination composition. The invention also provides methods of using said pharmaceutical composition, said extract(s), and/or said combination composition for the treatment and/or prevention of cardiac glycoside-responsive, especially oleandrin-responsive, disease(s), condition(s) or disorder(s). The invention also provides methods of administering said extract(s) and composition(s). The invention also provides methods of preparing said extract(s) and composition(s).

We have discovered that a dual extract composition advantageously provides a compositional profile different than that of any single extract composition. For example, the compositional profile of a combination composition (dual extract composition) comprising an ethanolic (or aqueous ethanolic) extract in combination with a subcritical $CO_2$ (with or without modifier) extract is different and better than the compositional profile of a single extract composition comprising said ethanolic extract, said subcritical $CO_2$ extract, a hot-water extract, a cold-water extract, or a supercritical $CO_2$ extract. A key advantage is that the combination composition is that, relative to the oleandrin content and the content of other components extractable from the biomass, it includes less of said other components, but it still comprises a substantial amount of oleandrin, the desired target pharmacologically active substance in said extracts. Moreover, the combination composition advantageously comprises more non-oleandrin components than any of the individual extracts and some of those non-oleandrin components are exhibit pharmacological activity.

As used herein, "plant material" is defined as a plant or plant part (e.g. bark, wood, leaves, branches, stems, roots, shoots, flowers, fruits, seeds, berries, or other plant parts) as well as exudates, and includes material falling within the definition of "botanical raw material" in the Guidance for Industry Botanical Drug Products Draft Guidance, August 2000, US Department of Health and Human Services, Food and Drug Administration Center for Drug Evaluation and Research. Cultured cellular mass may also be used as the plant material (biomass). Plant material is considered to be within the scope of biomass. In preferred embodiments, the plant material comprises leaves, shoots and/or stems.

Embodiments of the invention include those wherein the oleandrin-containing biomass (plant material) is *Nerium* sp., *Nerium oleander*, *Nerium oleander* L (Apocynaceae), *Nerium odourum*, *Nerium indicum*, white oleander, pink oleander, *Thevetia* sp., yellow oleander, *Agrobacterium tumefaciens* (Ibrahim et al., "Stimulation of oleandrin production by combined *Agrobacterium tumefaciens* mediated transformation and fungal elicitation in *Nerium oleander* cell cultures" in *Enz. Microbial Technol.* (2007), 41(3), 331-336, the entire disclosure of which is hereby incorporated by reference), cell culture of *Nerium* sp. (Ibrahim et al., "Enhancement of oleandrin production in suspension cultures of *Nerium oleander* by combined optimization of medium composition and substrate feeding" in *J. Plant Biosys.* (2009), 143(1), 97-103, the entire disclosure of which is hereby incorporated by reference), cell culture of *Thevetia* sp., or a combination thereof. *Nerium oleander* can be obtained from microculture in vitro, whereby shoot cultures can be initiated from seedlings and/or from shoot apices of the *Nerium oleander* cultivars *Splendens giganteum*, Revanche or Alsace, or other cultivars (Vila et al., "Micropropagation of Oleander (*Nerium oleander* L.)" in *HortScience* (2010), 45(1), 98-102, the entire disclosure of which is hereby incorporated by reference). *Nerium oleander* plant material can be obtained, for example, from commercial plant suppliers such as Aldridge Nursery, Atascosa, Texas. Suitable varietals of *Nerium oleander* include Album (white), Petit Salmon (pink), True Pale, Pink Beauty, Calypso (dark pink), or Red Hardy.

As used herein, the term "oleandrin" is taken to mean all known forms of oleandrin unless otherwise specified. Oleandrin can be present in racemic, optically pure, optically enriched form or stereoisomeric form.

As used herein, the term semi-volatile organic compound (SVOC) is organic compounds that possess Henry's law constants (H) in the range of $1\times10^{-5}$ to $3\times10^{-7}$ atm*m$^3$/mol* (* H range defined as volatility from liquid to air) and demonstrate higher boiling points, usually greater than that of water with correspondingly low vapor pressure from $10^{-14}$-$10^{-4}$ atm. As used herein, the term volatile organic compound (VOC) is any organic compound having an initial boiling point less than or equal to 250° C. measured at a standard atmospheric pressure of 101.3 kPa.

The organic solvent extract and the subcritical liquid extract comprise at least oleandrin, VOCs, and SVOCs, and said extracts can further comprise one or more nonvolatile organic compounds; therefore, a respective combination composition formed with said extracts comprises those components as well.

The invention provides a method of producing oleandrin or oleandrin-containing extract from oleandrin-containing biomass by a) subcritical liquid (SbCL) extraction (SbCLE) with carbon dioxide, optionally further comprising at least one modifier; b) extraction with organic solvent (OSE), optionally further comprising water; or c) a combination of ScCLE and OSE. The extractions can be conducted on the same biomass or on different batches of biomass.

FIG. 1 depicts a phase diagram for carbon dioxide indicating the solid, liquid, gas and supercritical fluid phases. SbCLE is conducted in the liquid phase region outside the supercritical fluid phase region (in a phase diagram) for carbon dioxide. The liquid phase region is bounded by the solid-liquid phase line, the liquid-gas phase line, the liquid-supercritical phase line, the supercritical fluid-liquid phase line, the triple point (solid-liquid-gas), and the critical point (liquid-gas-supercritical). The approximate critical point temperature and pressure for $CO_2$ are $t_{cp}$=about 31-31.1° C. and $p_{cp}$=about 73.7-73.8 bar, respectively. The approximate triple point temperature and pressure for $CO_2$ are $t_{tp}$=about −56.4-56.5° C. and $p_{tp}$=about 5.1-5.2 bar, respectively.

The subcritical extraction liquid primarily comprises $CO_2$; therefore, the determination of subcritical conditions is with respect to the known phase diagram(s) for carbon dioxide. Subcritical conditions are therefore achieved by performing the extraction under the following conditions in the extraction vessel: a) a temperature in the range of about −56.4° C. to about 31.1° C. or less; b) a pressure at or above 5.1 bar; and/or c) at a subcritical temperature and/or at a subcritical pressure for carbon dioxide, such that the extraction medium is in liquid phase rather than in solid, gas, or supercritical fluid phase. Accordingly, the SbCLE is conducted under pressure and temperature conditions wherein the extraction medium (comprising primarily carbon dioxide, and optionally comprising modifier) remains in the subcritical liquid phase rather than the gas phase, solid phase, or supercritical fluid phase.

The preferred extraction conditions are those wherein the subcritical liquid is at or above the critical pressure, above the triple point temperature, below the critical point temperature, and below the solid-liquid phase line. In reference to the phase diagram, the region bounded by those conditions provides a subcritical liquid of higher density, which results in higher extraction efficiency.

The extraction period is that period of time during which the extraction liquid and biomass are in contact. For the SbCLE, the extraction period, for each extraction cycle, typically ranges from 0.1 to 24 h, 0.5 to 12 h, or 0.5 to 6 h. For the organic solvent extraction, the extraction period, for each extraction cycle, typically ranges from 0.1 to 24 h, 0.5 to 12 h, or 0.5 to 6 h.

In some embodiments, the subcritical liquid comprises carbon dioxide. In other embodiments, the subcritical liquid comprises carbon dioxide and at least one modifier. The modifier can be alcohol, organic solvent, alkyl ketone, alkyl ester or a combination thereof. Particularly suitable modifiers include ethanol, methanol propanol, acetone, ethyl acetate, methyl ethyl ketone, glycol (e.g. propylene glycol), dimethyl sulfoxide (DMSO), N,N-dimethylformamide (DMF), or N-methylpyrrolidone (NMP).

The weight ratio of subcritical liquid to biomass may also affect extraction efficiency. In some embodiments the weight ratio of subcritical liquid (with or without modifier) to biomass is in the range of about 20:1 to about 100:1, about 30:1 to about 75:1, about 50:1, about 45:1 to 60:1, or about 40:1 to about 45:1, based on weight of both the solvent and the raw material.

During a major portion (about 50% or more) of the SbCL extraction period, the extraction fluid will be in subcritical liquid form (in the extraction milieu). In some embodiments, the extraction liquid will be in subcritical liquid form for at least 60%, at least 70%, at least 80%, at least 90%, at least 95%, or at least 99% of the extraction period. In some embodiments, the extraction liquid will be in subcritical liquid form throughout the extraction period.

Due to equipment performance, it is possible that carbon dioxide extraction of the biomass might occur in the supercritical phase for a short period of time; however, for a majority (about 50% or more) of the extraction period, the extraction will occur at subcritical conditions.

SbCLE of *Nerium* biomass was conducted according to Example 3. Dried biomass was extracted with subcritical liquid CO$_2$ (about 90-95 wt %) containing alcohol (ethanol, about 10-5 wt %, respectively). Following completion of the extraction time period, the extraction milieu biomass was separated from the subcritical liquid by filtration to provide the oleandrin-containing subcritical liquid (also comprising other extracted components). The CO$_2$ was vented to provide a crude extract which was diluted with ethanol, then frozen, then thawed, then filtered, then concentrated in vacuo, and once again diluted with 50% v/v aqueous ethanol.

The organic solvent extraction was performed according to Example 15. Dried and powdered *Nerium* biomass was extracted with aqueous ethanol (containing 10% v/v of water) three times (three extraction cycles). For each extraction cycle, the extraction milieu was filtered after completion of the extraction period. The respective three supernatant were combined and concentrated in vacuo to about 20% of the original volume to form a concentrate, which was sterile filtered, thereby forming the crude ethanolic extract, which was then diluted with 50% v/v/aqueous ethanol.

The composition (based upon the content of some known components) of the SbCL extract was compared to the composition of the prior art supercritical fluid (SCF) extract of *Nerium oleander* (PBI-05204, described above), the prior art hot water extract (ANVIRZEL™), and the organic solvent extract, prepared as described herein. Based upon the same amount of plant material, a) the yield of oleandrin (mg oleandrin per Kg of plant material) observed was ethanolic extract>subcritical extract>supercritical extract; b) the yield of VOC and SVOC (mg VOC+SVOC per Kg of plant material) observed was supercritical extract>ethanolic extract>subcritical extract. The content of the individual components may vary by ±25%, ±20%, ±15%, ±10% or ±5% relative to the values indicated. Standards of oleandrin, oleanolic acid, ursolic acid, betulinic acid and derivatives thereof can also be purchased from Sigma-Aldrich (www.sigmaaldrich.com; St. Louis, MO, USA).

The partial compositions of the extracts are determined by DART TOF-MS (Direct Analysis in Real Time Time of Flight Mass Spectrometry) on a JEOL AccuTOF-DART mass spectrometer (JEOL USA, Peabody, MA, USA).

In some embodiments, the extract comprises cardiac glycoside(s), glycone(s), aglycone(s), steroid(s), triterpene(s), polysaccharide(s), saccharide(s), alkaloid(s), fat, protein(s), or a combination thereof. Specific compounds include oleandrin and other compounds that may be present include neritaloside, odoroside, oleanolic acid, ursolic acid, betulinic acid, oleandrigenin, oleaside A, betulin (urs-12-ene-3☐,28-diol), 28-norurs-12-en-3☐-ol, urs-12-en-3☐-ol, 3☐,3☐-hydroxy-12-oleanen-28-oic acid, 3☐,20☐-dihydroxyurs-21-en-28-oic acid, 3☐,27-dihydroxy-12-ursen-28-oic acid, 3☐,13☐-dihydroxyurs-11-en-28-oic acid, 3☐,12☐-dihydroxyoleanan-28,13☐-olide, 3☐,27-dihydroxy-12-oleanan-28-oic acid, homopolygalacturonan, arabinogalaturonan, chlorogenic acid, caffeic acid, L-quinic acid, 4-coumaroyl-CoA, 3-O-caffeoylquinic acid, 5-O-caffeoylquinic acid, cardenolide B-1, cardenolide B-2, oleagenin, neridiginoside, nerizoside, odoroside-H, 3-beta-O-(D-diginosyl)-5-beta, 14 beta-dihydroxy-card-20(22)-enolide pectic polysaccharide composed of galacturonic acid, rhamnose, arabinose, xylose, and galactose, polysaccharide with MW in the range of 17000-120000 D, or MW about 35000 D, about 3000 D, about 5500 D, or about 12000 D, cardenolide monoglycoside, cardenolide N-1, cardenolide N-2, cardenolide N-3, cardenolide N-4, pregnane, 4,6-diene-3,12,20-trione, 20R-hydroxypregna-4,6-diene-3,12-dione, 16beta,17beta-epoxy-12beta-hydroxypregna-4,6-diene-3,20-dione, 12beta-hydroxypregna-4,6,16-triene-3,20-dione (neridienone A), 20S,21-dihydroxypregna-4,6-diene-3,12-dione (neridienone B), neriucoumaric acid, isoneriucoumaric acid, oleanderoic acid, oleanderen, 8alpha-methoxylabdan-18-oic acid, 12-ursene, kaneroside, neriumoside, 3β-O-(D-diginosyl)-2α-hydroxy-8,14β-epoxy-5β-carda-16:17, 20:22-dienolide, 3β-O-(D-diginosyl)-2α,14β-dihydroxy-5β-carda-16:17,20:22-dienolide, 3β,27-dihydroxy-urs-18-en-13,28-olide, 3β,22α,28-trihydroxy-25-nor-lup-1(10),20(29)-dien-2-one, cis-karenin (3β-hydroxy-28-Z-p-coumaroyloxy-urs-12-en-27-oic acid), trans-karenin (3-β-hydroxy-28-E-p-coumaroyloxy-urs-12-en-27-oic acid), 3beta-hydroxy-5alpha-carda-14(15),20(22)-dienolide (beta-anhydroepidigitoxigenin), 3 beta-O-(D-digitalosyl)-21-hydroxy-5beta-carda-8,14,16,20(22)-tetraenolide (neriumogenin-A-3beta-D-digitaloside), proceragenin, neridienone A, 3beta,27-dihydroxy-12-ursen-28-oic acid, 3beta,13beta-dihydroxyurs-11-en-28-oic acid, 3beta-hydroxyurs-12-en-28-aldehyde, 28-orurs-12-en-3beta-ol, urs-12-en-3beta-ol, urs-12-ene-3beta,28-diol, 3beta,27-dihydroxy-12-oleanen-28-oic acid, (20S, 24R)-epoxydammarane-3beta,25-diol, 20beta,28-epoxy-28alpha-methoxytaraxasteran-3beta-ol, 20beta,28-epoxytaraxaster-21-en-3beta-ol, 28-nor-urs-12-ene-3beta,17 beta-diol, 3beta-hydroxyurs-12-en-28-aldehyde, alpha-neriursate, beta-neriursate, 3alpha-acetophenoxy-urs-12-en-28-oic acid, 3beta-acetophenoxy-urs-12-en-28-oic acid, oleanderolic acid, kanerodione, 3β-p-hydroxyphenoxy-11α-methoxy-12α-hydroxy-20-ursen-28-oic acid, 28-hydroxy- 20(29)-lupen-3,7-dione, kanerocin, 3alpha-hydroxy-urs-18, 20-dien-28-oic acid, D-sarmentose, D-diginose, neridiginoside, nerizoside, isoricinoleic acid, gentiobiosyl-nerigoside, gentiobiosylbeaumontoside, gentiobiosyloleandrin, folinerin, 12β-hydroxy-5β-carda-8,14,16,20(22)-tetra-enolide, 8β-hydroxy-digitoxigenin, Δ16-8β-hydroxy-digitoxigenin, Δ16-neriagenin, uvaol, ursolic aldehyde, 27(p-coumaroyloxy)ursolic acid, oleanderol, 16-anhydro-deacteyl-nerigoside, 9-D-hydroxy-cis-12-octadecanoic acid, adigoside, adynerin, alpha-amyrin, beta-sitosterol, campestrol, caoutchouc, capric acid, caprylic acid, choline, cornerin, cortenerin, deacetyloleandrin, diacetyl-nerigoside, foliandrin, pseudocuramine, quercetin, quercetin-3-rhamnoglucoside, quercitrin, rosaginin, rutin, stearic acid, stigmasterol, strospeside, urehitoxin, and uzarigenin. Additional components that may be present in the extract are disclosed by Gupta et al. (*IJPSR* (2010), 1(3), 21-27, the entire disclosure of which is hereby incorporated by reference).

The identity of some of the volatile and semi-volatile organic compounds present in the organic solvent extract and the subcritical extract were determined by GS mass spectrometry analysis according to Example 18. The volatile and semivolatile compounds found in the ethanolic and/or subcritical extract were tentatively identified as 2, 3-dihydrobenzofuran, Squalene, 2-(Decanoyloxy)propane-1,3-diyl dioctanoate, Alpha tocopherol, Stigmasterol, Gamma-sitosterol, Decanoic acid, 1,2,3-propanetriyl ester, Ursolic aldehyde, catetchol, 5-hydroxymethylfural, (E)-4-(3-Hydroxy-prop-1-en-1-yl)-2-methoxyphenol, n-hexadecenoic acid, Bis (2-ethylhexyl) phthalate, 1,4-Benzenedicarboxylic acid, bis (2-ethylhexyl) ester, and Didecyl phthalate. Additional unidentified volatile and semi-volatile compounds were observed.

Figure 3:
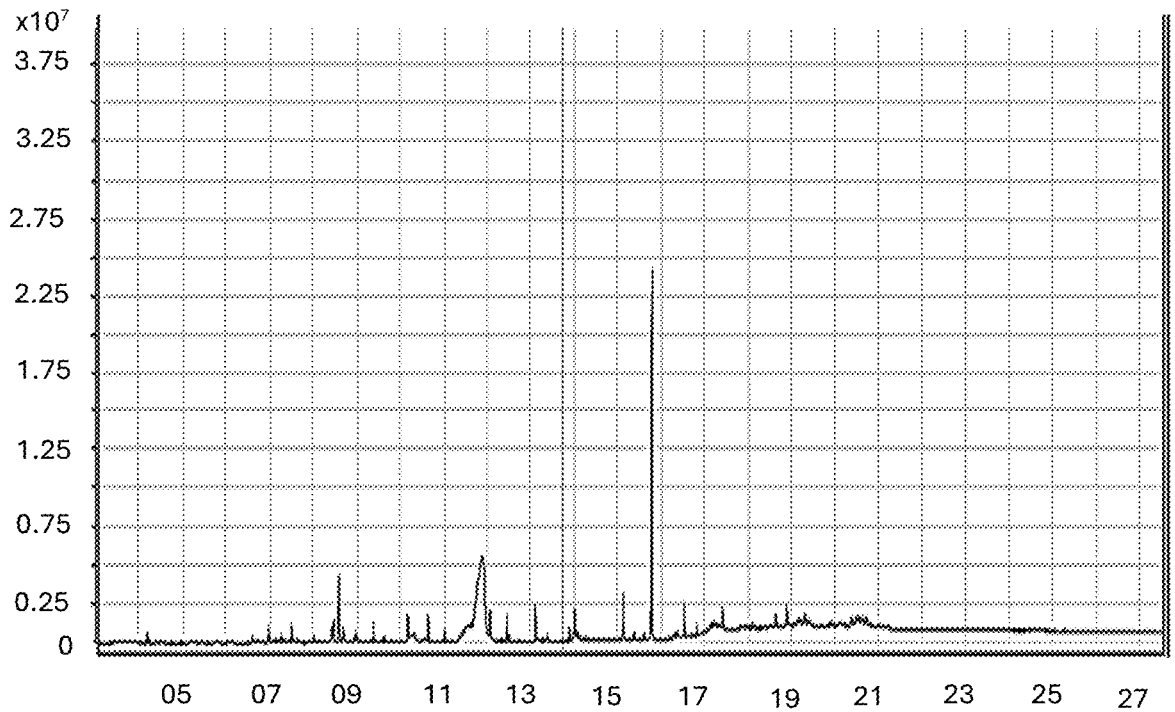
FIG. 3 depicts chromatograms from GC-mass spectrometry analysis, with total ion current (TIC) detection, of the ethanolic extract (top), the subcritical $CO_2$ extract (middle), and the prior art supercritical fluid extract PBI-05204 (bottom) determined according to Example 18. The data can be used to identify volatile and semi-volatile components of the extract.
Figure 3:
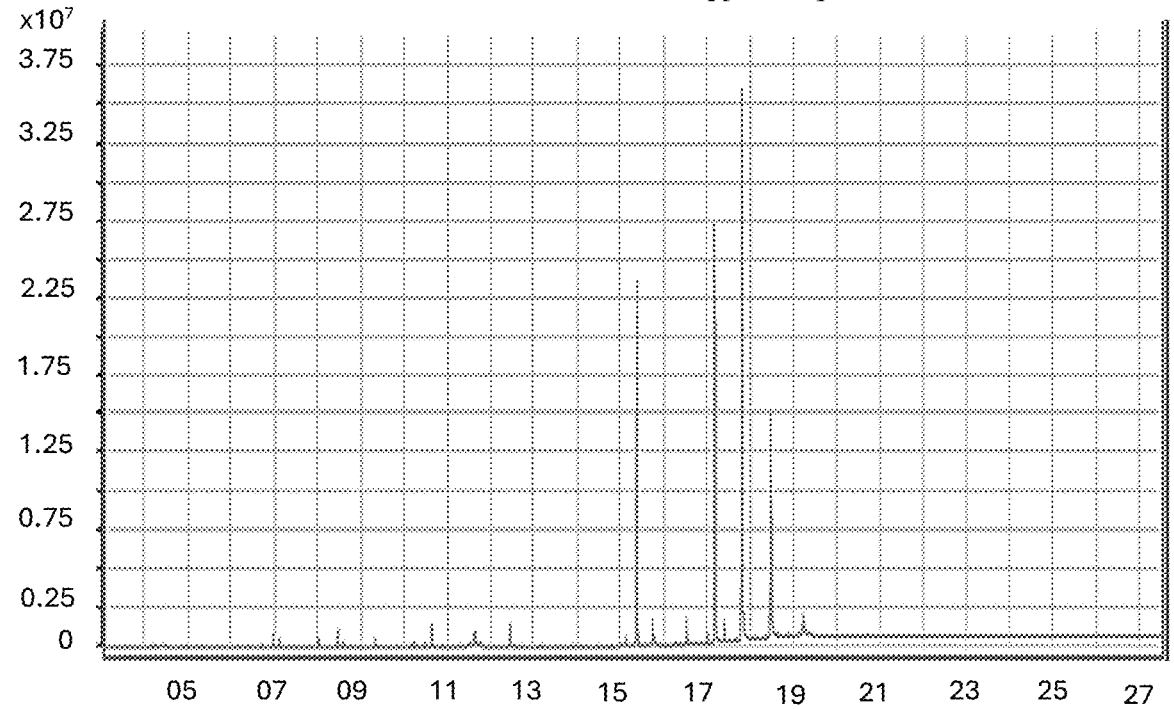
Figure 3:
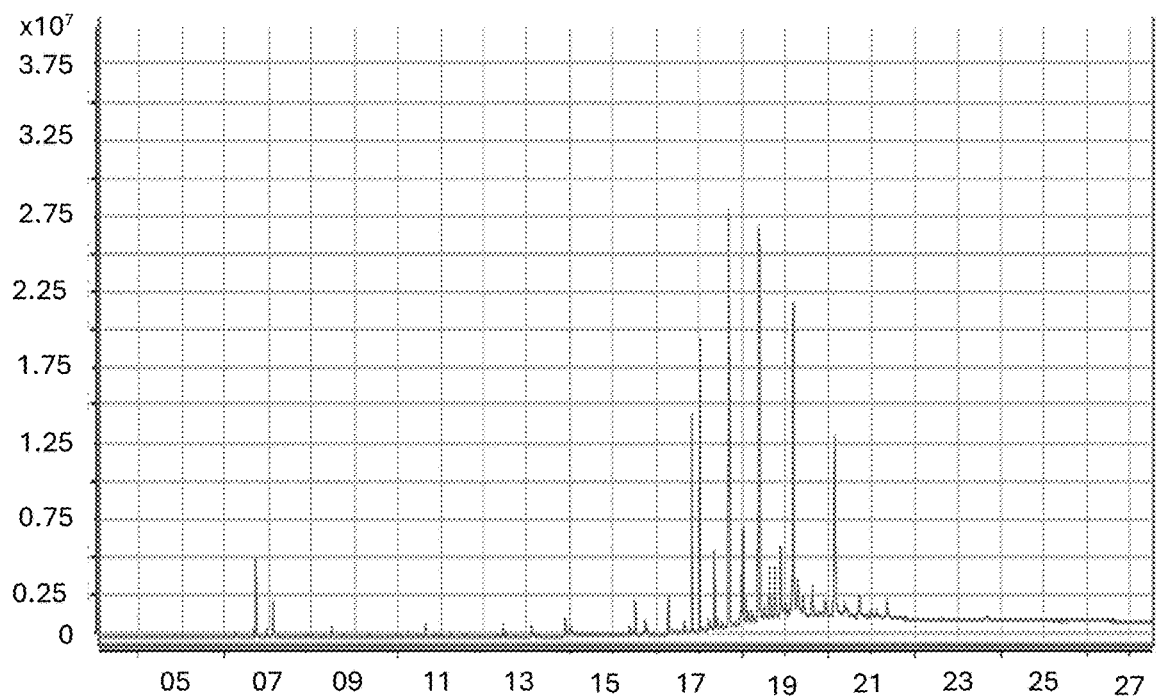

As evidenced by the GC chromatograms in FIG. 3, the compositional profiles of the ethanolic extract (top), the subcritical $CO_2$ extract (middle), and PBI-05204 differ. The ethanolic extract has fewer VOCs and SVOCs than the subcritical extract, and the subcritical extract has fewer VOCs and SVOCs than PBI-05204, the supercritical fluid extract. The combination composition comprising the ethanolic extract and the subcritical fluid extract thus has fewer VOCs and SVOCs than does PBI-05204.

The compositional profile of the organic solvent extract, the subcritical liquid extract, the combination composition, and PBI-05204 are also determined by HPLC, with tandem mass spectrometry detection and/or UV/VIS detection according to Example 10. The HPLC chromatograms indicate the combination composition has a compositional profile as would be predicted by mixing equal portions of the ethanolic extract and the SbCL extract and has a compositional profile different than that of PBI-05204. The content of oleandrin in each extract is quantified, whereby it is observed that the ethanolic extract has a much greater relative content of oleandrin, on an equal weight basis, than does the SbCL extract. Moreover, by use of internal standards for other components known to be present in *Nerium oleander* extracts, it is observed that content of oleandrin relative to those other components differs between the three extracts.

The composition of the organic solvent extract and SbCL extract differs according to the relative content of individual components therein. Based upon phytochemical analysis of the extracts, the composition of the individual extracts can be defined as follows in terms of the relative content of the classes (types) of components therein.

Extract made by ethanolic extraction: total free amino acids>total sugars>total cellulose>total alkaloids>total polyphenols~total flavonoids>total starch>total crude protein Extract made by aqueous ethanolic extraction: total free amino acids>total cellulose>total alkaloids>total sugars>total polyphenols~total flavonoids>total starch>total crude protein Extract made by SbCL extraction: total free amino acids>total starch>total alkaloids>total cellulose>total flavonoids>total sugars>total polyphenols>total crude protein Their compositions further differ based upon the relative content of terpenoids, cardiac glycosides and other components as follows.

Extract made by ethanolic extraction: kanerocin>kanerodione>oleanolic acid>ursolic acid~oleandrin~betulinic acid>oleandrigenin~*Nerium* F, odoroside (A and H)~adynerin~odoroside-G-acetate>gitoxigenin.

Extract made by SbCL extraction: oleanolic acid>ursolic acid~oleandrin~betulinic acid>oleandrigenin~*Nerium* F>odoroside (A and H)~adynerin~odoroside-G-acetate>kanerocin.

The combination composition may further comprise one or more of the following compounds obtained during extraction of biomass: neritaloside, neriin, folinerin, gitoxigenin, digitoxigenin, nerigoside, rutin, ursonic acid, neridienone A, adynerigenin, deacetyloleandrin, odoroside G acetate, and/or quercetin.

A subject treated with the SbCL extract, ethanolic extract, or combination composition according to the invention will exhibit a therapeutic response. By "therapeutic response" is meant that the subject will enjoy at least one of the following clinical benefits as a result of treatment: reduction of severity of symptoms, reduction in the occurrence of symptoms, partial or full remission, and/or healing. The therapeutic response can be a full or partial therapeutic response.

Dietary ingredients and food substances that can be included in the nutraceutical composition are listed by the U.S.F.D.A. (https://www.fda.gov/food/new-dietary-ingredients-ndi-notification-process/new-dietary-ingredients-dietary-supplements-background-industry, https://www.accessdata.fda.gov/scripts/fdcc/?set=FoodSubstances, and https://www.accessdata.fda.gov/scripts/fdcc/?cat=foodingredpkg, the entire disclosure of which are hereby incorporated by reference). Exemplary classes of dietary ingredients or food substances include vitamin, mineral, herb, botanical, amino acid, protein, fat, polynucleotide, polysaccharide, carbohydrate, lipid, VOC, SVOC, antioxidant, phenolic compound, flavorant, essence, aromatic compound, water, sweetener, leavening agent, flavor enhancer, coloring agent, emulsifier, preservative, anti-caking agent, salt, buffer, oil, grain, enzyme, hormone, lecithin, melanin, polymer, biopolymer, fiber, starch, fatty acid, any substance found in any food, concentrate thereof, metabolite thereof, or extract thereof.

Inactive ingredients that can be added to the compositions of the invention are listed by the U.S.F.D.A. (https://www.fda.gov/drugs/drug-approvals-and-databases/inactive-ingredients-database-download, the entire disclosure of which is hereby incorporated by reference).

A dosing regimen includes a therapeutically relevant dose (or effective dose) of oleandrin (in extract or composition) administered according to a dosing schedule. A therapeutically relevant dose, therefore, is a therapeutic dose at which a therapeutic response is observed and at which a subject can be administered the oleandrin without an excessive amount of unwanted or deleterious side effects. A therapeutically relevant dose is non-lethal to a subject, even though it may cause some side effects in the patient. It is a dose at which the level of clinical benefit to a subject being administered the oleandrin exceeds the level of deleterious side effects experienced by the subject due to administration of the oleandrin.

A cosmetic (cosmeceutical) composition may include one or more cosmetic excipients such as those approved by the U.S.F.D.A. (https://www.fda.gov/cosmetics/cosmetic-products-ingredients/cosmetic-ingredients).

A cosmeceutical can further comprise one or more active ingredients and/or one or more excipients including, by way of example and without limitation, Acai oil, Alpha-lipoic acid, Green tea extract, Retinol, Coenzyme Q10 (CoQ10), Caffeine, Alpha-hydroxy Acids (AHAs), Hyaluronic Acid, Glycerin, Sorbitol, Mono and Diglycerides, White Mineral Oil (Petroleum Hydrocarbon Oil), Glyceryl Stearate, Propylene Glycol, Vitamin E, Citric Acid, Propyl Gallate, other known compounds, and combinations thereof.

Compositions and dosage forms of the invention can further comprise one or more pharmaceutically acceptable, nutraceutically, and/or cosmetically acceptable excipients. Dosage forms can comprise one or more excipients independently selected at each occurrence from the group consisting of acidic agent, alkaline agent, buffer, tonicity modifier, osmotic agent, water soluble polymer, water-swellable polymer, thickening agent, complexing agent, chelating agent, penetration enhancer. Suitable excipients include U.S.F.D.A. inactive ingredients approved for use in parenteral or oral formulations (dosage forms), such as those listed in the U.S.F.D.A.'s "Inactive Ingredients Database (available on the following website: https://www.fda.gov/Drugs/InformationOnDrugs/ucm113978.htm; October 2018), the entire disclosure of which is hereby incorporated by reference.

A therapeutically relevant dose will vary from subject to subject according to a variety of established pharmacologic, pharmacodynamic and pharmacokinetic principles. However, a therapeutically relevant dose (relative, for example, to oleandrin) will typically be about 1 or more microg per day, about 5 or more microg per day, about 10 or more microg per day, about 20 or more microg per day, about 25 or more microg per day, about 50 or more microg per day, about 75 or more microg per day, about 100 or more microg per day, about 200 or more microg per day, about 250 or more microg per day, about 500 or more microg per day, or up to about 750 microg of oleandrin per day or it can be in the range of about 1 to about 750 microg of oleandrin per dose, or might not exceed about 25 microg, about 100 microg, about 250 microg, about 500 microg, or about 750 microg of oleandrin/day. The actual amount of oleandrin required to provide a target therapeutic result in a subject may vary from subject to subject according to the basic principles of pharmacy. It will be understood that the specific dose level for any patient will depend upon a variety of factors including the indication being treated, severity of the indication, patient health, age, gender, weight, diet, pharmacological response, the specific dosage form employed, and other such factors.

In some embodiments, the subject is administered 140 microg to 315 microg per day of oleandrin. In some embodiments, a dose comprises 5 microg to 750 microg, 12 microg to 300 microg, or 12 microg to 120 microg of oleandrin. A recommended daily dose of oleandrin is generally about 0.25 to about 60 microg twice daily, about 5 to about 60 microg twice daily, about 5 to 30 microg twice daily. The dose can be about 0.5 to about 100 microg/day, about 1 to about 80 microg/day, about 1.5 to about 60 microg/day, about 1.8 to about 60 microg/day, about 5 to about 60 microg/day. The minimum effective dose can be about 0.5 microg/day, about 1 microg/day, about 1.5 microg/day, about 1.8 microg/day, about 2 microg/day, or about 5 microg/day. Suitable doses comprising oleandrin can be about 0.05-0.5 mg/kg/day, about 0.05-0.35 mg/kg/day, about 0.05-0.22 mg/kg/day, about 0.05-0.4 mg/kg/day, about 0.05-0.3 mg/kg/day, about 0.05-0.5 microg/kg/day, about 0.05-0.35 microg/kg/day, about 0.05-0.22 microg/kg/day, about 0.05-0.4 microg/kg/day, or about 0.05-0.3 microg/kg/day. In some embodiments, the dose of oleandrin is about 1 mg to about 0.05 mg, about 0.9 mg to about 0.07 mg, about 0.7 mg to about 0.1 mg, about 0.5 mg to about 0.1 mg, about 0.4 mg to about 0.1 mg, about 0.3 mg to about 0.1 mg, about 0.2 mg. The invention includes all combinations of the doses set forth herein.

The recommended daily dose of oleandrin, present in the extract, can be about 0.1 microg to about 4.5 microg/kg body weight twice daily. The dose of oleandrin can be about 0.1 to about 1 microg/kg body weight/day, about 0.5 to about 1.0 microg/kg body weight/day, about 0.75 to about 1.5 microg/kg body weight/day, about 1.5 to about 2.52 microg/kg body weight/day, about 2.5 to about 3.0 microg/kg body weight/day, about 3.0 to 4.0 microg/kg body weight/day or about 3.5 to 4.5 microg oleandrin/kg body weight/day.

The oleandrin can be present in a dosage form in an amount sufficient to provide a subject with an initial dose of oleandrin of about 20 to about 100 microg, about 12 microg to about 300 microg, or about 12 microg to about 120 microg. A dosage form can comprise about 1 microg of oleandrin to about 100 microg, about 0.01 microg to about 100 mg or about 0.01 microg to about 100 microg oleandrin, oleandrin extract or extract of *Nerium oleander* containing oleandrin.

In some embodiments, the concentration of oleandrin in the plasma of a treated subject is about 10 microg/mL or less, about 5 microg/mL or less, about 2.5 microg/mL or less, about 2 microg/mL or less, or about 1 microg/mL or less. In some embodiments, the concentration of oleandrin in the plasma of a treated subject is about 0.0001 microg/mL or more, about 0.0005 microg/mL or more, about 0.001 microg/mL or more, about 0.0015 microg/mL or more, about 0.01 microg/mL or more, about 0.015 microg/mL or more, about 0.1 microg/mL or more, about 0.15 microg/mL or more, about 0.05 microg/mL or more, or about 0.075 microg/mL or more. In some embodiments, the concentration of oleandrin in the plasma of a treated subject is about 10 microg/mL to about 0.0001 microg/mL, about 5 microg/mL to about 0.0005 microg/mL, about 1 microg/mL to about 0.001 microg/mL, about 0.5 microg/mL to about 0.001 microg/mL, about 0.1 microg/mL to about 0.001 microg/mL, about 0.05 microg/mL to about 0.001 microg/mL, about 0.01 microg/mL to about 0.001 microg/mL, about 0.005 microg/mL to about 0.001 microg/mL. The invention includes all combinations and selections of the plasma concentration ranges set forth herein.

Based on human clinical data it is anticipated that 50% to 75% of an administered dose of oleandrin will be orally bioavailable therefore providing about 10 to about 20 microg, about 20 to about 40 microg, about 30 to about 50 microg, about 40 to about 60 microg, about 50 to about 75 microg, about 75 to about 100 microg of oleandrin per dosage form. Given an average blood volume in adult humans of 5 liters, the anticipated oleandrin plasma concentration will be in the range of about 0.05 to about 2 ng/ml, about 0.005 to about 10 ng/mL, about 0.005 to about 8 ng/mL, about 0.01 to about 7 ng/mL, about 0.02 to about 7 ng/mL, about 0.03 to about 6 ng/mL, about 0.04 to about 5 ng/mL, or about 0.05 to about 2.5 ng/mL.

A therapeutically relevant dose can be administered according to any dosing regimen typically used in the treatment of viral infection. A therapeutically relevant dose can be administered once, twice, thrice or more daily. It can be administered every other day, every third day, every fourth day, every fifth day, semiweekly, weekly, biweekly, every three weeks, every four weeks, monthly, bimonthly, semimonthly, every three months, every four months, semi-annually, annually, or according to a combination of any of the above to arrive at a suitable dosing schedule. For example, a therapeutically relevant dose can be administered one or more times daily (up to 10 times daily for the highest dose) for one or more weeks. A total daily dose may also be administered by infusion or pump over several hours, throughout part of a day, or throughout a 12 to 24 h period.

The invention also provides a method of treatment by repeatedly administering to a subject in need thereof plural therapeutically effective doses of oleandrin (in an oleandrin-containing composition of the invention). One or more doses may be administered per day for one or more days per week and optionally for one or more weeks per month and optionally for one or more months per year.

In some embodiments, one or more doses of oleandrin (oleandrin-containing composition or oleandrin-containing extract) are administered per day for plural days until the desired clinical endpoint(s). In some embodiments, one or more doses of oleandrin (oleandrin-containing composition or oleandrin-containing extract) are administered per day for plural days and plural weeks until the until the desired clinical endpoint(s). One or more doses can be administered in a day. One, two, three, four, five, six or more doses can be administered per day. Oleandrin (oleandrin-containing composition or oleandrin-containing extract) can be administered chronically, i.e. on a recurring basis, such as daily, every other day, every second day, every third day, every fourth day, every fifth day, every sixth day, weekly, every other week, every second week, every third week, monthly, bimonthly, semi-monthly, every other month every second month, quarterly, every other quarter, trimesterly, seasonally, semi-annually and/or annually. The treatment period may be one or more weeks, one or more months, one or more quarters and/or one or more years. An effective dose of oleandrin (oleandrin-containing composition or oleandrin-containing extract) is administered one or more times in a day. Oleandrin (oleandrin-containing composition or oleandrin-containing extract) can be administered one or more times per day for two or more days per week, optionally for one or more weeks per month and optionally for one or more months per year.

In general, a subject is evaluated to determine whether said subject is in need of oleandrin therapy. Administration of oleandrin-containing extract is then indicated. Initial doses of the extract are administered to the subject according to a prescribed dosing regimen for a period of time (a treatment period). The subject's clinical response and level of therapeutic response are determined periodically. If the level of therapeutic response is too low at one dose, then the dose is escalated according to a predetermine dose escalation schedule until the desired level of therapeutic response in the subject is achieved. Treatment of the subject with oleandrin is continued as needed. The dose or dosing regimen can be adjusted as needed until the patient reaches the desired clinical endpoint(s) such as cessation of a condition, reduction in symptoms, and/or a reduction in the progression of a condition.

If a clinician intends to treat a subject having with a combination of oleandrin-containing extract and one or more other therapeutic agents, then the present method invention comprises: administering to the subject in need thereof a therapeutically relevant dose of oleandrin and a therapeutically relevant dose of said one or more other therapeutic agents, wherein the oleandrin is administered according to a first dosing regimen and the one or more other therapeutic agents is administered according to a second dosing regimen. In some embodiments, the first and second dosing regimens are the same. In some embodiments, the first and second dosing regimens are different.

Oleandrin can be administered as primary therapy, adjunct therapy, or co-therapy. Methods of the invention include separate administration or coadministration of oleandrin with at least one other therapeutic agent, meaning oleandrin can be administered before, during or after administration of said other therapeutic agent.

The one or more other therapeutic agents can be administered at doses and according to dosing regimens that are clinician-recognized as being therapeutically effective or at doses that are clinician-recognized as being sub-therapeutically effective. The clinical benefit and/or therapeutic effect provided by administration of a combination of oleandrin and one or more other therapeutic can be additive or synergistic, such level of benefit or effect being determined by comparison of administration of the combination to administration of the individual component(s). The one or more other therapeutic agents can be administered at doses and according to dosing regimens as suggested or described by the Food and Drug Administration, World Health Organization, European Medicines Agency (E.M.E.A.), Therapeutic Goods Administration (TGA, Australia), Pan American Health Organization (PAHO), Medicines and Medical Devices Safety Authority (Medsafe, New Zealand) or the various Ministries of Health worldwide.

The antiviral activity of the SbCL extract, ethanolic extract, and combination composition is established according to Example 7, wherein in vitro assays set forth in WO 2018053123 A1, WO 2019055119 A1, U.S. Ser. No. 10/596, 186 B2, and related U.S. and foreign patents and applications, the entire disclosures of all of which are hereby incorporated by reference in their entirety, are followed to demonstrate the antiviral activity of a composition of the invention. Treatable viral infections include those from viruses of the Arenaviridae family, Arteriviridae, Bunyaviridae family, Filoviridae family, Flaviviridae family (Flavivirus genus), Orthomyxoviridae family (influenza virus genus), Paramyxoviridae family, Rhabdoviridae family, Retroviridae family (*Deltaretrovirus* genus), Coronaviridae family, (+)-ss-envRNAV (positive sense single stranded enveloped RNA virus), (−)-ss-envRNAV (negative sense single stranded enveloped RNA virus), or Togaviridae family, as well as any of their known genera, species, and/or strains. In some embodiments, the (+)-ss-envRNAV is a coronavirus that is pathogenic to humans. Specific viruses that can be treated include, at least, Ebolavirus, Marburgvirus, Alphavirus, Flavivirus, Yellow Fever, Dengue Fever, Japanese Encephalitis, West Nile Viruses, Zikavirus, Venezuelan Equine Encephalomyelitis (encephalitis) (VEE) virus, Chikungunya virus, Western Equine Encephalomyelitis (encephalitis) (WEE) virus, Eastern Equine Encephalomyelitis (encephalitis) (EEE) virus, Tick-borne Encephalitis, Kyasanur Forest Disease, Alkhurma Disease, Omsk Hemorrhagic Fever, Hendra virus, Nipah virus, *Deltaretrovirus* genus, HTLV-1 virus, coronavirus, SARS-CoV, MERS-CoV, COVID-19 (SARS-CoV-2), CoV 229E, CoV NL63, CoV OC43, CoV HKU1, CoV HKU20, O'nyong'nvirus (ONNV), Pogosta disease virus, Sindbis virus, Ross River fever virus (RRV), Semliki Forest virus, Lassa virus, aseptic meningitis, Guanarito virus, Junin virus, Lujo virus, Machupo virus, Sabia virus, Whitewater Arroyo virus, Hantavirus, Crimean-Congo hemorrhagic fever orthonairovirus, mumps virus, Nipah virus, Hendra virus, respiratory syncytial virus (RSV), human parainfluenza virus (HPIV), NDV (Newcastle disease virus), influenza virus (A through C), Isavirus, Thogotovirus, Quaranjavirus, H1N1 virus, H2N2 virus, H3N2 virus, H1N2 virus, Spanish flu virus, Asian flu virus, Hong Kong Flu virus, Russian flu virus, rabies virus, vesiculovirus, Lyssavirus, and Cytorhabdovirus.

The neuroprotective activity of the SbCL extract, ethanolic extract, and combination composition is established according to Example 8, wherein the in vitro assays set forth in WO 2011085307 A1, U.S. Pat. No. 8,481,086 B2, U.S. Pat. No. 9,220,778 B2, U.S. Pat. No. 9,358,293 B2, U.S. Pat. No. 9,877,979 B2, U.S. Ser. No. 10/383,886 B2, and related U.S. and foreign patents and applications, the entire disclosures of all of which are hereby incorporated by reference in their entirety, are followed to demonstrate the neuroprotective activity of a composition of the invention.

The anticancer (anti-excessive cell proliferation) activity of the SbCL extract, ethanolic extract, and combination composition is established according to Example 11, wherein the in vitro assays set forth in WO 2007016176A2, WO 2009064657 A1, U.S. Pat. No. 7,402,325 B2, U.S. Pat. No. 8,187,644 B2, U.S. Pat. No. 8,394,434 B2, U.S. Pat. No. 8,367,363 B2, U.S. Pat. No. 9,494,589 B2, U.S. Pat. No. 9,846,156 B2, and related U.S. and foreign patents and applications, the entire disclosures of all of which are hereby incorporated by reference in their entirety, are followed to demonstrate the anticancer activity of a composition of the invention.

Said condition, disease or disorder that is therapeutically responsive to oleandrin (oleandrin-containing composition or oleandrin-containing extract) can be selected from the group consisting of cancer, tumor, carcinoma, sarcoma, glioblastoma, adenocarcinoma, lymphoma, melanoma, brain tumor, glioma, astrocytoma (which include low-grade astrocytomas (Grade I pilocytic astrocytoma, and Grade II diffuse astrocytoma), anaplastic astrocytoma (Grade III), glioblastoma (Grade IV, GBM, also known as glioblastoma multiforme)), ependymoma, oligodendroglioma, excessive cell proliferation, malignant neoplastic disease, noncancerous inflammatory skin diseases, actinic keratosis, psoriasis, eczema, neurological disease, neurological disorders, neurodegenerative disease, neurodegenerative disorder, neurological disease or disorder having an etiology associated with altered Na,K-ATPase activity, Alzheimer's disease, Parkinson's disease, Huntington's disease, stroke, dementia, amyotrophic lateral sclerosis, bovine spongiform encephalopathy, multiple sclerosis, diabetic neuropathy, autism and juvenile neuronal ceroid lipofuscinosis, tauopathy, Down's syndrome, Pick's disease, corticobasal degeneration, some variants of prions disease, progressive supranuclear palsy, frontotemporal dementia, hemorrhoids, ulcer, leprosy, snake bite, warts, or viral infection.

Compound(s) present in the composition of the invention can be present in their unmodified form, salt form, derivative form or a combination thereof. As used herein, the term "derivative" is taken to mean: a) a chemical substance that is related structurally to a first chemical substance and theoretically derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps. For example, a derivative may include a deuterated form, oxidized form, dehydrated, unsaturated, polymer conjugated or glycosilated form thereof or may include an ester, amide, lactone, homolog, ether, thioether, cyano, amino, alkylamino, sulfhydryl, heterocyclic, heterocyclic ring-fused, polymerized, pegylated, benzylidenyl, triazolyl, piperazinyl or deuterated form thereof.

As used herein, the individually named compounds can independently be selected upon each occurrence in their native (unmodified, free acid, or free base) form, in their salt form, in derivative form, prodrug form, or a combination thereof. Compositions containing and methods employing deuterated forms of the triterpenes are also within the scope of the invention.

The oleandrin-containing extract (composition) can be formulated in any suitable pharmaceutically acceptable dosage form. Suitable types of dosage forms include aerosol, bar, bead, capsule, cellular sheet, chewable, cloth, concentrate, cream, crystal, disc, douche, dressing, elixir, emulsion, enema, fiber, film, foam, gel, globule, granule, gum, implant, inhalable, injectable, injection, insert, intrauterine device, jelly, kit, liniment, lipstick, liposome(s), liquid, lotion, lozenge, mouthwash, oil, ointment, paste, pastille, patch, pellet, plaster, poultice, powder, lyophilized powder, ring, rinse, salve, shampoo, soap, solution, sponge, spray, stick, strip, suppository, swab, suspension, syrup, tablet, tampon, tape, tincture, troche, wafer or other such dosage forms known to the artisan of ordinary skill in the pharmaceutical sciences.

The oleandrin-containing extract (composition) can be included in an oral dosage form. Some embodiments of the dosage form are not enteric coated and release their charge of extract within a period of 0.5 to 1 hours or less. Some embodiments of the dosage form are enteric coated and release their charge of extract downstream of the stomach, such as from the jejunum, ileum, small intestine, and/or large intestine (colon). Enterically coated dosage forms will release extract into the systemic circulation within 1-10 hr after oral administration.

The oleandrin-containing extract (composition) can be included in a rapid release, immediate release, controlled release, sustained release, prolonged release, extended release, burst release, continuous release, slow release, or pulsed release dosage form or in a dosage form that exhibits two or more of those types of release. The release profile of oleandrin from the dosage form can be a zero order, pseudo-zero, first order, pseudo-first order or sigmoidal release profile. The plasma concentration profile for oleandrin in a subject to which it is administered can exhibit one or more maxima.

Suitable dosage forms can also be made according to U.S. Pat. No. 8,187,644 B2 to Addington, which issued May 29, 2012, U.S. Pat. No. 7,402,325 B2 to Addington, which issued Jul. 22, 2008, U.S. Pat. No. 8,394,434 B2 to Addington et al, which issued Mar. 12, 2013, the entire disclosures of which are hereby incorporated by reference. Suitable dosage forms can also be made as described in Examples 4-6, and 9.

The oleandrin-containing extract (or any composition comprising it) may be administered locally, systemically or both. Suitable modes of administration include parenteral, buccal, conjunctival, corneal, cutaneous, dental, endocervical, endosinusial, endotracheal, enteral, epidermal, epidural, extra-amniotic, extracorporeal, infiltration, interstitial, intra-abdominal, intra-amniotic, intra-arterial, intrabronchial, intrabursal, intracardiac, intracavernous, intracavitary, intracerebral, intracorneal, intramuscular, intradermal, intradiscal, intraduodenal, intradural, intraepidermal, intraesophageal, intragastric, intraileal, intraluminal, intralymphatic, intrameningeal, intramedullary, intraocular, intraovarian, intrapericardial, intraperitoneal, intrapleural, intraprostatic, intrapulmonary, intrasinal, intrasynovial, intratesticular, intrathecal, intrathoracic, intratubular, intratumor, intrauterine, intravascular, intravenous, intraventricular, intravesical, intravitreal, irrigation, laryngeal, nasal, nasogastric, ocular, ophthalmic, oral, otic (auricular), oropharyngeal, parenteral, percutaneous, periarticular, peridural, perineural, periodontal, peroral, pulmonary, rectal, retrobulbar, subarachnoid, subconjunctival, subcutaneous, subdermal, sublingual, submucosal, topical, transdermal, transmucosal, transplacental, transtracheal, transtympanic, ureteral, urethral, vaginal, or other known mode of administration.

It should be noted that a compound herein might possess one or more functions in a composition or formulation of the invention. For example, a compound might serve as both a surfactant and a water miscible solvent or as both a surfactant and a water immiscible solvent.

A liquid composition can comprise one or more pharmaceutically acceptable liquid carriers. The liquid carrier can be an aqueous, non-aqueous, polar, non-polar, and/or organic carrier. Liquid carriers include, by way of example and without limitation, a water miscible solvent, water immiscible solvent, water, buffer and mixtures thereof.

As used herein, the terms "water soluble solvent" or "water miscible solvent", which terms are used interchangeably, refer to an organic liquid which does not form a biphasic mixture with water or is sufficiently soluble in water to provide an aqueous solvent mixture containing at least five percent of solvent without separation of liquid phases. The solvent is suitable for administration to humans or animals. Exemplary water soluble solvents include, by way of example and without limitation, PEG (poly(ethylene glycol)), PEG 400 (poly(ethylene glycol having an approximate molecular weight of about 400), ethanol, acetone, alkanol, alcohol, ether, propylene glycol, glycerin, triacetin, poly(propylene glycol), PVP (poly(vinyl pyrrolidone)), dimethylsulfoxide, N,N-dimethylformamide, formamide, N,N-dimethylacetamide, pyridine, propanol, N-methylacetamide, butanol, soluphor (2-pyrrolidone), pharmasolve (N-methyl-2-pyrrolidone).

As used herein, the terms "water insoluble solvent" or "water immiscible solvent", which terms are used interchangeably, refer to an organic liquid which forms a biphasic mixture with water or provides a phase separation when the concentration of solvent in water exceeds five percent. The solvent is suitable for administration to humans or animals. Exemplary water insoluble solvents include, by way of example and without limitation, medium/long chain triglycerides, oil, castor oil, corn oil, vitamin E, vitamin E derivative, oleic acid, fatty acid, olive oil, softisan 645 (Diglyceryl Caprylate/Caprate/Stearate/Hydroxy stearate adipate), miglyol, captex (Captex 350: Glyceryl Tricaprylate/Caprate/Laurate triglyceride; Captex 355: Glyceryl Tricaprylate/Caprate triglyceride; Captex 355 EP/NF: Glyceryl Tricaprylate/Caprate medium chain triglyceride).

Suitable solvents are listed in the "International Conference on Harmonisation of Technical Requirements for Registration of Pharmaceuticals for Human Use (ICH) guidance for industry *Q3C Impurities: Residual Solvents*" (1997), which makes recommendations as to what amounts of residual solvents are considered safe in pharmaceuticals. Exemplary solvents are listed as class 2 or class 3 solvents. Class 3 solvents include, for example, acetic acid, acetone, anisole, 1-butanol, 2-butanol, butyl acetate, tert-butlymethyl ether, cumene, ethanol, ethyl ether, ethyl acetate, ethyl formate, formic acid, heptane, isobutyl acetate, isopropyl acetate, methyl acetate, methyl-1-butanol, methylethyl ketone, methylisobutyl ketone, 2-methyl-1-propanol, pentane, 1-pentanol, 1-propanol, 2-propanol, or propyl acetate.

Other materials that can be used as water immiscible solvents in the invention include: Captex 100: Propylene Glycol Dicaprate; Captex 200: Propylene Glycol Dicaprylate/Dicaprate; Captex 200 P: Propylene Glycol Dicaprylate/Dicaprate; Propylene Glycol Dicaprylocaprate; Captex 300: Glyceryl Tricaprylate/Caprate; Captex 300 EP/NF: Glyceryl Tricaprylate/Caprate Medium Chain Triglycerides; Captex 350: Glyceryl Tricaprylate/Caprate/Laurate; Captex 355: Glyceryl Tricaprylate/Caprate; Captex 355 EP/NF: Glyceryl Tricaprylate/Caprate Medium Chain Triglycerides; Captex 500: Triacetin; Captex 500 P: Triacetin (Pharmaceutical Grade); Captex 800: Propylene Glycol Di (2-Ethythexanoate); Captex 810 D: Glyceryl Tricaprylate/Caprate/Linoleate; Captex 1000: Glyceryl Tricaprate; Captex CA: Medium Chain Triglycerides; Captex MCT-170: Medium Chain Triglycerides; Capmul GMO: Glyceryl Monooleate; Capmul GMO-50 EP/NF: Glyceryl Monooleate; Capmul MCM: Medium Chain Mono- & Diglycerides; Capmul MCM C8: Glyceryl Monocaprylate; Capmul MCM C10: Glyceryl Monocaprate; Capmul PG-8: Propylene Glycol Monocaprylate; Capmul PG-12: Propylene Glycol Monolaurate; Caprol 10G100: Decaglycerol Decaoleate; Caprol 3GO: Triglycerol Monooleate; Caprol ET: Polyglycerol Ester of Mixed Fatty Acids; Caprol MPGO: Hexaglycerol Dioleate; Caprol PGE 860: Decaglycerol Mono-, Dioleate.

As used herein, a "surfactant" refers to a compound that comprises polar or charged hydrophilic moieties as well as non-polar hydrophobic (lipophilic) moieties; i.e., a surfactant is amphiphilic. The term surfactant may refer to one or a mixture of compounds. A surfactant can be a solubilizing agent, an emulsifying agent or a dispersing agent. A surfactant can be hydrophilic or hydrophobic.

The hydrophilic surfactant can be any hydrophilic surfactant suitable for use in pharmaceutical compositions. Such surfactants can be anionic, cationic, zwitterionic or non-ionic, although non-ionic hydrophilic surfactants are presently preferred. As discussed above, these non-ionic hydrophilic surfactants will generally have HLB values greater than about 10. Mixtures of hydrophilic surfactants are also within the scope of the invention.

Similarly, the hydrophobic surfactant can be any hydrophobic surfactant suitable for use in pharmaceutical compositions. In general, suitable hydrophobic surfactants will have an HLB value less than about 10. Mixtures of hydrophobic surfactants are also within the scope of the invention.

Examples of additional suitable solubilizer include: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide); amides, such as 2-pyrrolidone, 2-piperidone, caprolactam, N-alkylpyrrolidone, N-hydroxyalkylpyrrolidone, N-alkylpiperidone, N-alkylcaprolactam, dimethylacetamide, and polyvinypyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, caprolactone and isomers thereof, valerolactone and isomers thereof, butyrolactone and isomers thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol nonoethyl ether (available from Gattefosse under the trade name Transcutol), and water. Mixtures of solubilizers are also within the scope of the invention.

Except as indicated, compounds mentioned herein are readily available from standard commercial sources.

Although not necessary, the composition or formulation may further comprise one or more chelating agents, one or more preservatives, one or more antioxidants, one or more adsorbents, one or more acidifying agents, one or more alkalizing agents, one or more antifoaming agents, one or more buffering agents, one or more colorants, one or more electrolytes, one or more salts, one or more stabilizers, one or more tonicity modifiers, one or more diluents, or a combination thereof.

The composition of the invention can also include oils such as fixed oils, peanut oil, sesame oil, cottonseed oil, corn oil and olive oil; fatty acids such as oleic acid, stearic acid and isostearic acid; and fatty acid esters such as ethyl oleate, isopropyl myristate, fatty acid glycerides, medium chain triglycerides, and acetylated fatty acid glycerides. The composition can also include alcohol such as ethanol, isopropanol, hexadecyl alcohol, glycerol and propylene glycol; glycerol ketals such as 2,2-dimethyl-1,3-dioxolane-4-methanol; ethers such as poly(ethylene glycol) 450; petroleum hydrocarbons such as mineral oil and petrolatum; water; a pharmaceutically suitable surfactant, suspending agent or emulsifying agent; or mixtures thereof.

It should be understood that the compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

One or more of the components of the formulation can be present in its free base, free acid or pharmaceutically or analytically acceptable salt form. As used herein, "pharmaceutically or analytically acceptable salt" refers to a compound that has been modified by reacting it with an acid as needed to form an ionically bound pair. Examples of acceptable salts include conventional non-toxic salts formed, for example, from non-toxic inorganic or organic acids. Lists of suitable salts are found in *Remington's Pharmaceutical Sciences,* 17$^{th}$. ed., Mack Publishing Company, Easton, PA, 1985, p. 1418, the relevant disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with tissues of human beings and animals and without excessive toxicity, irritation, allergic response, or any other problem or complication, commensurate with a reasonable benefit/risk ratio.

A dosage form can be made by any conventional means known in the pharmaceutical industry. A liquid dosage form can be prepared by providing at least one liquid carrier and oleandrin (oleandrin-containing composition, SbCL extract) in a container. One or more other excipients can be included in the liquid dosage form. A solid dosage form can be prepared by providing at least one solid carrier and oleandrin. One or more other excipients can be included in the solid dosage form.

A dosage form can be packaged using conventional packaging equipment and materials. It can be included in a pack, bottle, via, bag, syringe, envelope, packet, blister pack, box, ampoule, or other such container.

The composition of the invention can be included in any dosage form. Particular dosage forms include a solid or liquid dosage forms. Exemplary suitable dosage forms include tablet, capsule, pill, caplet, troche, sache, and other such dosage forms known to the artisan of ordinary skill in the pharmaceutical sciences.

In view of the above description and the examples below, one of ordinary skill in the art will be able to practice the invention as claimed without undue experimentation. The foregoing will be better understood with reference to the following examples that detail certain procedures for the preparation of embodiments of the present invention. All references made to these examples are for the purposes of illustration. The following examples should not be considered exhaustive, but merely illustrative of only a few of the many embodiments contemplated by the present invention.

Example 1

Supercritical Fluid Extraction of Powdered Oleander Leaves

Comparative Example

Method A. With Carbon Dioxide.

Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.94 kg.

The starting material was combined with pure $CO_2$ at a pressure of 300 bar (30 MPa, 4351 psi) and a temperature of 50° C. (122° F.) in an extractor device. A total of 197 kg of $CO_2$ was used, to give a solvent to raw material ratio of 50:1. The mixture of $CO_2$ and raw material was then passed through a separator device, which changed the pressure and temperature of the mixture and separated the extract from the carbon dioxide.

The extract (65 g) was obtained as a brownish, sticky, viscous material having a nice fragrance. The color was likely caused by chlorophyll and other residual chromophore compounds. For an exact yield determination, the tubes and separator were rinsed out with acetone and the acetone was evaporated to give an addition 9 g of extract. The total extract amount was 74 g. Based on the weight of the starting material, the yield of the extract was 1.88%. The content of oleandrin in the extract was calculated using high pressure liquid chromatography and mass spectrometry to be 560.1 mg, or a yield of 0.76%.

Method B. With Mixture of Carbon Dioxide and Ethanol Powdered oleander leaves were prepared by harvesting, washing, and drying oleander leaf material, then passing the oleander leaf material through a comminuting and dehydrating apparatus such as those described in U.S. Pat. Nos. 5,236,132, 5,598,979, 6,517,015, and 6,715,705. The weight of the starting material used was 3.85 kg.

The starting material was combined with pure $CO_2$ and 5% ethanol as a modifier at a pressure of 280 bar (28 MPa, 4061 psi) and a temperature of 50° C. (122° F.) in an extractor device. A total of 160 kg of $CO_2$ and 8 kg ethanol was used, to give a solvent to raw material ratio of 43.6 to 1. The mixture of $CO_2$, ethanol, and raw material was then passed through a separator device, which changed the pressure and temperature of the mixture and separated the extract from the carbon dioxide.

The extract (207 g) was obtained after the removal of ethanol as a dark green, sticky, viscous mass obviously containing some chlorophyll. Based on the weight of the starting material, the yield of the extract was 5.38%. The content of oleandrin in the extract was calculated using high pressure liquid chromatography and mass spectrometry to be 1.89 g, or a yield of 0.91%.

Example 2

Hot-Water Extraction of Powdered Oleander Leaves

Comparative Example

Hot water extraction is typically used to extract oleandrin and other active components from oleander leaves. Examples of hot water extraction processes can be found in U.S. Pat. Nos. 5,135,745 and 5,869,060.

A hot water extraction was carried out using 5 g of powdered oleander leaves. Ten volumes of boiling water (by weight of the oleander starting material) were added to the powdered oleander leaves and the mixture was stirred constantly for 6 hours. The mixture was then filtered and the leaf residue was collected and extracted again under the same conditions. The filtrates were combined and lyophilized. The appearance of the extract was brown. The dried extract material weighed about 1.44 g. 34.21 mg of the extract material was dissolved in water and subjected to oleandrin content analysis using high pressure liquid chromatography and mass spectrometry. The amount of oleandrin was determined to be 3.68 mg. The oleandrin yield, based on the amount of extract, was calculated to be 0.26%.

Example 3

Preparation of Subcritical Fluid Extract of *Nerium oleander*

An improved process for the preparation of an oleandrin-containing extract was developed by employing subcritical liquid extraction rather than supercritical fluid extraction of *Nerium oleander* biomass.

Dried and powdered biomass (prepared according to Example 14) was placed in an extraction chamber, which was then sealed. Carbon dioxide (about 90-95% wt) and alcohol (about 10-5% wt; methanol or ethanol) were injected into the chamber. The interior temperature and pressure of the chamber were such that the extraction medium was maintained in the subcritical liquid phase, rather than the supercritical fluid phase, for a majority or substantially all of the extraction time period: Temperature in the range of about 2° C. to about 16° C. (about 7° C. to about 8° C.), and pressure in the range of about 115 to about 135 bar (about 124 bar). The extraction period was about 4 h to about 12 h (about 6 to about 10 h). The extraction milieu was then filtered and the supernatant collected. The carbon dioxide was vented from the supernatant, and the resulting crude extract was diluted into ethanol (about 9 parts ethanol:about 1 part extract) and frozen at about −50° C. for at least 12 h. The solution was thawed and filtered (100 micron pore size filter). The filtrate was concentrated to about 10% of its original volume and then sterile filtered (0.2 micron pore size filter). The concentration of oleandrin in the crude extract is about 0.25 to 1 mg (or 0.5 to 0.8 mg) per mL of extract.

The resulting subcritical liquid (SbCL) extract comprised oleandrin and one or more other compounds extractable from *Nerium oleander*, said one or more other compounds being as defined herein.

Example 4

Sublingual/Buccal Liquid Dosage Form

A sublingual dosage form comprising oleandrin was made by mixing oleandrin or oleandrin-containing composition (e.g. oleandrin-containing extract) with medium chain triglyceride (MCT, e.g. coconut oil).

Method A. The ethanol diluted SbCL extract (2 wt %) was mixed with MCT (95 wt %), and flavoring agent (3 wt %).

Method B. The ethanol diluted ethanolic extract (2 wt %) was mixed with MCT (95 wt %), and flavoring agent (3 wt %).

Method C. The ethanol diluted SbCL extract (1 wt %) was mixed with the ethanol diluted ethanolic extract (1 wt %), MCT (95 wt %), and flavoring agent (3 wt %).

The sublingual dosage form was safely administered to a subject by about 0.5 mL aliquots. No beverage or food was consumed for at least ten minutes after administration. It was administered one to six times daily for about seven days to about one month.

Even though intended for sublingual administration, this dosage form may also be administered orally.

Example 5

Preparation of Pharmaceutical Compositions

Method A. Cremophor-Based Drug Delivery System

The following ingredients are provided in the amounts indicated.

| Reagent Name | Function | Percent of Formulation (% w/w) |
| --- | --- | --- |
| SbCL extract | Active agent | 3.7 |
| Vitamin E | Antioxidant | 0.1 |
| Labrasol | Surfactant | 9.2 |
| Ethanol | Co-solvent | 9.6 |
| Cremophor EL | Surfactant | 62.6 |
| Cremophor RH40 | Surfactant | 14.7 |

The excipients are dispensed into a jar and shook in a New Brunswick Scientific C24KC Refrigerated Incubator shaker for 24 hours at 60° C. to ensure homogeneity. The samples are then pulled and visually inspected for solubilization.

Both the excipients and antiviral composition are totally dissolved for all formulations after 24 hours.

Method B. GMO/Cremophor-Based Drug Delivery System

The following ingredients are provided in the amounts indicated.

| Reagent Name | Function | Percent of Formulation (% w/w) |
| --- | --- | --- |
| SbCL extract | Active agent | 4.7 |
| Vitamin E | Antioxidant | 0.1 |
| Labrasol | Surfactant | 8.5 |
| Ethanol | Co-solvent | 7.6 |
| Cremophor EL | Surfactant | 56.1 |
| Glycerol Monooleate | Surfactant | 23.2 |

The procedure of Method A is followed.

Method C. Labrasol-Based Drug Delivery System

The following ingredients are provided in the amounts indicated.

| Reagent Name | Function | Percent of Formulation (% w/w) |
| --- | --- | --- |
| SbCL extract | Active agent | 3.7 |
| Vitamin E | Antioxidant | 0.1 |
| Labrasol | Surfactant | 86.6 |
| Ethanol | Co-solvent | 9.6 |

The procedure of Method A is followed.

Method D. Vitamin E-TPGS Based Micelle Forming System

The following ingredients are provided in the amounts indicated.

| Component | Function | Weight % (w/w) |
| --- | --- | --- |
| Vitamin E | Antioxidant | 1.0 |
| Vitamin E TPGS | Surfactant | 95.2 |
| SbCL extract | Active agent | 3.8 |

The procedure of Method A is followed.

Method E. Multi-Component Drug Delivery System

The following ingredients are provided in the amounts indicated.

| Component | Weight (g) | Weight % (w/w) |
| --- | --- | --- |
| Vitamin E | 10.0 | 1.0 |
| Cremophor ELP | 580.4 | 55.9 |
| Labrasol | 89.0 | 8.6 |
| Glycerol Monooleate | 241.0 | 23.2 |
| Ethanol | 80.0 | 7.7 |
| SbCL extract | 38.5 | 3.7 |
| Total | 1038.9 | 100 |

The procedure of Method A is followed.

Method F. Multi-Component Drug Delivery System

The following ingredients are provided in the amounts indicated an included in a capsule.

| Component | Tradename | Weight % (w/w) |
| --- | --- | --- |
| SbCL extract | | 0.6 |
| Vitamin E | FLAVEX Naturextrakte | 1.3 |
| Caprylocaproyl polyoxy glycerides | Labrasol Gattefosse 3074TPD | 11.1 |
| Lauroyl polyoxy glycerides | Gelucire 44/14 Gattefosse 3061TPD | 14.6 |
| Polyoxyl 35 Castor oil | Kolliphor BASF Corp. 50251534 | 72.4 |
| Total | | 100 |

The procedure of Method A is followed.

Example 6

Preparation of Enteric Coated Capsules

Step I: Preparation of Liquid-Filled Capsule

Hard gelatin capsules (50 counts, 00 size) are filled with a liquid composition of Example 3. These capsules are manually filled with 800 mg of the formulation and then sealed by hand with a 50% ethanol/50% water solution. The capsules are then banded by hand with 22% gelatin solution containing the following ingredients in the amounts indicated.

| Ingredient | Wt. (g) |
| --- | --- |
| Gelatin | 140.0 |
| Polysorbate 80 | 6.0 |
| Water | 454.0 |
| Total | 650.0 |

The gelatin solution is mixed thoroughly and allowed to swell for 1-2 hours. After the swelling period, the solution is covered tightly and placed in a 55° C. oven and allowed to liquefy. Once the entire gelatin solution is liquid, the banding is performed Using a pointed round 3/0 artist brush, the gelatin solution is painted onto the capsules. Banding kit provided by Shionogi is used. After the banding, the capsules are kept at ambient conditions for 12 hours to allow the band to cure.

Step II: Coating of Liquid-Filled Capsule

A coating dispersion is prepared from the ingredients listed in the table below.

| Ingredient | Wt. % | Solids % | Solids (g) | g/Batch |
| --- | --- | --- | --- | --- |
| Eudragit L30D55 | 40.4 | 60.5 | 76.5 | 254.9 |
| TEC | 1.8 | 9.0 | 11.4 | 11.4 |
| AlTale 500V | 6.1 | 30.5 | 38.5 | 38.5 |
| Water | 51.7 | na | na | 326.2 |
| Total | 100.0 | 100.0 | 126.4 | 631.0 |

If banded capsules according to Step I are used, the dispersion is applied to the capsules to a 20.0 mg/cm² coating level. The following conditions are used to coat the capsules.

| Parameters | Set-up |
|---|---|
| Coating Equipment | Vector LDCS-3 |
| Batch Size | 500 g |
| Inlet Air Temp. | 40° C. |
| Exhaust Air Temp. | 27-30° C. |
| Inlet Air Volume | 20-25 CFM |
| Pan Speed | 20 rpm |
| Pump Speed | 9 rpm (3.5 to 4.0 g/min) |
| Nozzle Pressure | 15 psi |
| Nozzle diameter | 1.0 mm |
| Distance from tablet bed* | 2-3 in |

*Spray nozzle iss set such that both the nozzle and spray path are under the flow path of inlet air.

Example 7

Treatment of Viral Infection in a Subject

The methods of WO 2018053123 A1, WO 2019055119 A1, U.S. Ser. No. 10/596,186 B2, and related U.S. and foreign patents and applications, the entire disclosures of all of which are hereby incorporated by reference in their entirety, are followed to demonstrate the antiviral activity of a composition of the invention.

Example 8

Treatment of Neurological Disorder in a Subject

The methods of WO 2011085307 A1, U.S. Pat. No. 8,481,086 B2, U.S. Pat. No. 9,220,778 B2, U.S. Pat. No. 9,358,293 B2, U.S. Pat. No. 9,877,979 B2, U.S. Ser. No. 10/383,886 B2, and related U.S. and foreign patents and applications, the entire disclosures of all of which are hereby incorporated by reference in their entirety, are followed to demonstrate the neuroprotective activity of a composition of the invention.

Example 9

Preparation of a Tablet Comprising Oleandrin Composition

An initial tabletting mixture of 3% Syloid 244FP and 97% microcrystalline cellulose (MCC) is mixed. Then, an existing batch of SbCL extract is incorporated into the Syloid/MCC mixture via wet granulation. This mixture is labeled "Initial Tabletting Mixture) in the table below. Additional MCC is added extra-granularly to increase compressibility. This addition to the Initial Tabletting Mixture is labeled as "Extra-granular Addition." The resultant mixture from the extra-granular addition is the same composition as the "Final Tabletting Mixture."

| Component | Weight (g) | Weight % (w/w) |
|---|---|---|
| Initial Tabletting Mixture | | |
| Microcrystalline cellulose | 48.5 | 74.2 |
| Colloidal Silicon Dioxide/Syloid 244FP | 1.5 | 2.3 |
| SbCL extract | 15.351 | 23.5 |
| Total | 65.351 | 100.0 |

Extragranular Addition

| Component | Weight (g) | Weight % (w/w) |
|---|---|---|
| Initial Tabulating Mixture | 2.5 | 50.0 |
| Microcrystalline cellulose | 2.5 | 50.0 |
| Total | 5 | 100.0 |

Final Tabletting Mixture: Abbreviated

| Component | Weight (g) | Weight % (w/w) |
|---|---|---|
| Microcrystalline cellulose | 4.36 | 87.11 |
| Colloidal Silicon Dioxide/Syloid 244FP | 0.06 | 1.15 |
| SbCL extract | 0.59 | 11.75 |
| Total | 5.00 | 100 |

Final Tabletting Mixture: Detailed

| Component | Weight (g) | Weight % (w/w) |
|---|---|---|
| Microcrystalline cellulose | 4.36 | 87.11 |
| Colloidal Silicon Dioxide/Syloid 244FP | 0.06 | 1.15 |
| Vitamin E | 0.01 | 0.11 |
| Cremophor ELP | 0.33 | 6.56 |
| Labrasol | 0.05 | 1.01 |
| Glycerol Monooleate | 0.14 | 2.72 |
| Ethanol | 0.05 | 0.90 |
| SbCL extract | 0.02 | 0.44 |
| Total | 5.00 | 100.00 |

Syloid 244FP is a colloidal silicon dioxide manufactured by Grace Davison. Colloidal silicon dioxide is commonly used to provide several functions, such as an adsorbant, glidant, and tablet disintegrant. Syloid 244FP is chosen for its ability to adsorb 3 times its weight in oil and for its 5.5 micron particle size.

Example 10

HPLC Analysis of Solutions Containing Oleandrin

Oleandrin Content:

Samples (oleandrin standard, SCF extract, ethanolic extract, subcritical liquid $CO_2$ extract, and hot-water extract) are analyzed on HPLC (Waters) using the following conditions: Symmetry C18 column (5.0 μm, 150×4.6 mm I.D.; Waters); Mobile phase of MeOH:water=54:46 (v/v) and flow rate at 1.0 ml/min. Detection wavelength was set at 217 nm. The samples are prepared by dissolving the compound or extract in a fixed amount of HPLC solvent to achieve an approximate target concentration of oleandrin. The retention time of oleandrin can be determined by using an internal standard. The concentration of oleandrin can be determined/calibrated by developing a signal response curve using the internal standard.

Figure 4:
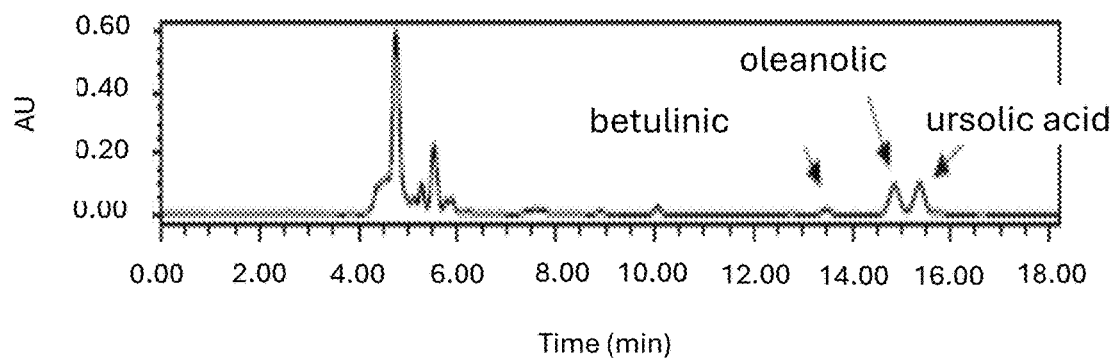
FIG. 4 depicts the HPLC chromatogram of PBI-05204 (prior art) whereby oleandrin is resolved from oleanolic acid, ursolic acid, and betulinic acid.

Triterpene Content:

The triterpene components of the extracts are quantified by HPLC using a Gemini C18 diphenyl column and eluting the triterpenes with an isocratic mobile phase consisting of 95% MeCN with 0.1% formic acid at a flow rate of 0.6 ml/min and a detection wavelength of 220 nm. Standard curves are developed and used to calculate the relative molar ratios of oleanolic acid, ursolic acid and betulinic acid compounds. FIG. 4 depicts the HPLC chromatogram of PBI-05204.

Example 11

Treatment of Cancer in a Subject

The methods of WO 2007016176A2, WO 2009064657 A1, U.S. Pat. No. 7,402,325 B2, U.S. Pat. No. 8,187,644 B2, U.S. Pat. No. 8,394,434 B2, U.S. Pat. No. 8,367,363 B2, U.S. Pat. No. 9,494,589 B2, U.S. Pat. No. 9,846,156 B2, and related U.S. and foreign patents and applications, the entire disclosures of all of which are hereby incorporated by reference in their entirety, were followed to demonstrate the anticancer (anti-excessive cell proliferation) activity of a composition of the invention.

Example 12

Preparation of Pharmaceutical Composition

A pharmaceutical composition of the invention can be prepared any of the following methods. Mixing can be done under wet or dry conditions. The pharmaceutical composition can be compacted, dried or both during preparation. The pharmaceutical composition can be portioned into dosage forms.
Method A.
At least one pharmaceutical excipient is mixed with at least one SbCL extract disclosed herein.
Method B.
At least one pharmaceutical excipient is mixed with at least SbCL extract and at least one other active agent.
Method C.
At least one pharmaceutical excipient is mixed with oleandrin.
Method D.
At least one pharmaceutical excipient is mixed with oleandrin and at least one triterpene disclosed herein.
Method E.
At least one pharmaceutical excipient is mixed with oleandrin and at least two triterpenes disclosed herein.
Method D.
At least one pharmaceutical excipient is mixed with oleandrin and at least three triterpenes disclosed herein.

Known amounts of oleanolic acid and ursolic acid are mixed according to a predetermined molar ratio of the components as defined herein. The components are mixed in solid form or were mixed in solvent(s), e.g. methanol, ethanol, chloroform, acetone, propanol, dimethyl sulfoxide (DMSO), dimethylformamide (DMF), dimethylacetamide (DMAC), N-methylpyrrolidone (NMP), water or mixtures thereof. The resultant mixture contains the components in the relative molar ratios as described herein.

Example 13

Statistical Analysis

The statistical significance of experimental data sets is determined using unpaired two-tailed Student's t-tests (alpha=0.05) and calculated P-values using the Shapiro-Wilk normality test and Graphpad Prism 7.03 software. The P-values are defined as: 0.1234 (ns), 0.0332 (*), 0.0021 (), 0.0002 (*), <0.0001 (****). Unless otherwise noted, error bars represent the SEM from at least three independent experiments.

Example 14

Preparation of Powdered Biomass

Method A.
Powdered and dried *Nerium oleander* biomass was prepared according to U.S. Pat. No. 7,402,325 B2 to Addington, the entire disclosure of which is hereby incorporated by reference, by placing harvested leaves in a comminuting and heated dehydrating apparatus as described in U.S. Pat. Nos. 5,236,132, 5,598,979, 6,517,015, or 6,715,705, the entire disclosures of which is hereby incorporated by reference.
Method B.
Powdered and dried *Nerium oleander* biomass was prepared by dehydrating harvested leaves in a heated dehumidifier and then subjecting the dried leaves to repeated freeze-thaw cycles with liquid nitrogen, during which at least one of the cycles the frozen leaves were comminuted to form a powder, which was then freeze dried to a moisture content of less than about 8 wt %.

Example 15

Preparation of Aqueous Organic Solvent Extract

An ethanolic extract of *Nerium oleander* was prepared by extracting dried powdered biomass with aqueous ethanol.
For each gram of leaf powder, 10 mL of aqueous ethanol (10% v/v water) was used to extract the powder while stirring vigorously at ambient temperature and pressure. The extraction supernatant and biomass were separated, and the extraction cycle was repeated two more times, meaning three extraction cycles were performed. The supernatants were combined and concentrated in vacuo to about 20% of the original volume to form a concentrate that was sterile filtered (0.2 micron filter) to form the crude extract, which was then diluted with 50% aqueous ethanol. The content of water, ethanol, and other components in the crude extract was determined. The content of oleandrin in the crude extract was about 1-5 mg/mL of extract.

Example 16

Preparation of Dosage Form Comprising a Combination of Extracts of *Nerium oleander*

The purpose of this was to prepare a dosage form according to Example 4 except that a portion (1 wt %) of the ethanolic extract or aqueous ethanolic extract is combined with a portion (1 wt %) of the SbCL extract of Example 3, medium chain triglyceride (95 wt %), and flavoring agent (3 wt %). The concentration of oleandrin in the dosage form is about 12.5 to about 25 microg/mL.

Example 17

In Vivo Evaluation of Oleandrin Against COVID-19 Virus

The purpose of this study was to determine the efficacy of oleandrin-containing extract (OCE) in treating subjects already infected with COVID-19 virus.

More than thirty subjects representing a broad demographic distribution and presenting with COVID-19 infection were evaluated to determine clinical status prior to sublingual, buccal or peroral administration of OCE, prepared according to the dosage form of Example 16. The composition was safely administered to subjects. The dosing regimen was approximately 0.5 mL per dose and four doses per day (one dose about every six hours), which approximates about 50-60 microg of oleandrin per day. All subjects experienced a complete recovery within three to ten days of initiation of treatment.

Example 18

Gas Chromatographic Analysis of Extract(s)

The organic solvent extract and the subcritical extract were analyzed by GC-mass spectrometry analysis, with total ion current (TIC) detection to identify some of the volatile and semi-volatile organic components thereof.

Sample extracts were dissolved using a solution containing seven isotopically labeled semi-volatile organic compound internal standards (SVOCIS) prior to being injected and analyzed by GC-MS. Ten largest peaks from each of the sample extracts were tentatively identified via comparison to the NIST/EPA/NIH Mass Spectral Library (NIST, 2014), and each match was manually checked. A library score for each identity was assigned by the software, where a match factor of 100 would indicate a perfect match. Relative concentrations for each of the identified peaks were calculated via peak area comparisons with its closest eluting SVOCIS standard peak. It should be noted that ionization efficiencies within the GC-MS can vary drastically between compounds.

Example 19

Identification of Compounds in Extracts

The extract is analyzed by MS-DART TOF analysis as follows. A JEOL AccuTOF-DART mass spectrometer (Jeol U.S.A., Peobody, MA, U.S.A.) was used.

A JEOL AccuTOF-DART mass spectrometer (Jeol USA, Peabody, MA, USA) was used. Analyses are conducted in a positive ion mode (DART+) giving masses corresponding to the M+H+ ions generated by the DART-MS. A range of settings on the instrument is used to determine optimal conditions for *N. oleander* analyses. The general settings for DART+ include: needle voltage 3500 V; orifice 1—2-20 V; ring lens 2-5 V; orifice 2—2-5 V; and peaks voltage 1000 V. Calibrations are performed internally with each sample using a 10% solution of PEG 600 which provides mass markers throughout the required mass range of 100-1000 mass units. Other analyses are undertaken in the DART-mode and these consisted of: needle voltage 3500 V; heating element 250° C.; electrode 1—150 V; electrode 2—250 V; He gas flow rate 3.79 LPM. Mass spectrometer settings: MCP 2600 V; orifice 1—15 V; ring lens—5 V, orifice 2—5 V; and peaks voltage 1000 V. Calibrations are performed internally with each sample using a perfluorinated carboxylic acid solution that provides markers throughout the required mass range of 100-1000 mass units. The *N. oleander* samples are introduced neat into the DART helium plasma using the closed end of a borosilicate glass melting point tube. The capillary tube is held in the He plasma for approximately 3-5 s per analysis. Molecular formulas are confirmed by elemental composition and isotope matching programs provided with the JEOL AccuTOF DART-MS instrument. A searchable database of *N. oleander* constituents developed by Herbal Science (Naples, FL, USA) can be used.

Example 20

Nutraceutical Composition

Oleandrin-containing extract (at the desired concentration) is combined with nutraceutical excipients such as those found in PREMIER PROTEIN shake, SLIMFAST ADVANCED ENERGY meal replacement shake, ORGAIN ORGANIC NUTRITION shake, VEGA Protein Nutrition shake, LEAN BODY LABRADA Whey protein meal replacement shake, ICONIC GRASS-FED protein drink, PURE PROTEIN shake, MUSCLE MILK original protein shake, MET-RX original whey protein meal replacement powder, OWYN vegan meal replacement shake, SOYLENT meal replacement shake, or APRES plant-based vegan protein shake.

Example 21

Cosmetic Lotion Composition

Oleandrin-containing extract (at the desired concentration) is combined with nutraceutical excipients such as those found in NIVEA ESSENTIALLY ENRICHED body lotion (with moisturizer serum and almond oil), EUCERIN ADVANCED REPAIR (with Ceramide-3), PALMER'S COCOA BUTTER FORMULA DAILY SKIN THERAPY both lotion (with cocoa butter and vitamin E), JERGEN'S ULTRA-HEALING dry skin moisturizer (with vitamins C, E, and B5), LUBRIDERM daily moisture body lotion (with vitamin B5), WELEDA SKIN FOOD nourishing cream (with vitamin E, calendula flower extract, pansy), AVEENO daily moisturizing lotion, HEMPZ original herbal body moisturizer (with hemp seed oil), CERAVE daily moisturizing lotion (with hyaluronic acid), AQUAPHOR ADVANCED THERAPY healing ointment (with petrolatum).

Example 22

Dosage Forms

Method A: Thin Film Dosage Form

A thin-film dosage form can be prepared according to Barnhart ("Thin film oral dosage forms" in Modified Release Drug Delivery Technology; $2^{nd}$ Edition, 2013, CRC press; ISBN: 9780429145803); Joshua et al. ("Fast dissolving oral thin films: an effective dosage form for quick releases" in Int. J. Pharm. Sci. Rev. Res. (2016), 38(1), 282-289), Harsha et al. ("An introduction to fast dissolving oral thin film drug delivery systems: a review" in Drug. Deliv. (2013), 10(6), 667-684), and Nagaraju et al. ("Comprehensive review on oral disintegrating films" in Drug Deliv. (2013), 10(1), 96-108).

Method B: Bioadhesive Dosage Form

A bioadhesive buccal dosage form can be prepared according to Reddy et al. ("A review on bioadhesive buccal drug delivery systems: current status of formulation and evaluation methods" in Daru (2011), 19(6), 385-403), Shojaei et al. ("Buccal mucosa as a route for systemic drug delivery: a review" in J. Pharm. Pharmaceut. Sci. (1998), 1(1), 15-30), Prabhakar et al. ("Bioadhesive polymeric platforms for transmucosal drug delivery systems—a review" in Trop. J. Pharma. Res. (2010), 9(1), 91-104), Mathiowitz et al. (Bioadhesive Drug Delivery Systems—fundamentals, novel approaches, and development; ed. E. Mathiowitz, et al.; Marcel Dekker, Inc. (New York, NY), (1999), ISBN 0-8247-1995-6).

Method C: Gummy Dosage Form

A gummy (semi-solid, soft, chewable) dosage form can be prepared according to Jacobs ("Semi-solid formulations" in Pediatric Form. (2014), 171-179), Cizauskaite et al. ("Natural ingredients-based gummy bear composition designed according to texture analysis and sensory evaluation in vivo" in Molecules (2019), 24(7), 1442), Bartkiene et al. ("Development of antimicrobial gummy candies with addition of bovine colostrum, essential oils, and probiotics" in Int. J. Food Sci. Technol. (2018), 53(5), 1227-1235).

Method D: Spray Dosage Form

Spray dosage forms can be prepared according to Finlay (The Mechanics of Inhaled Pharmaceutical Aerosols—An Introduction; Ed. W. H. Finlay, Academic Press, London, UK; 2001), Hickey ("Back to the Future: Inhaled Drug Products" in J. Pharm. Sci. (2013), 102(40), 1165-1172), Malamatari et al. ("Solidification of nanosuspensions for the production of solid oral dosage forms and inhalable dry powders" in Exp. Opin. Drug Deliv. (2016), 13(3), 435-450), and Hickey (Pharmaceutical Inhalation Aerosol Technology, $2^{nd}$ ed.; Ed. A. J. Hickey, CRC Press, New York, NY, 2003).

Example 23

Preparation of Organic Solvent Extract

An ethanolic extract of *Nerium oleander* was prepared by extracting dried powdered biomass with ethanol.

For each gram of leaf powder, 10 mL of ethanol was used to extract the powder while stirring vigorously at ambient temperature and pressure. The extraction supernatant and biomass were separated, and the extraction cycle was repeated two more times, meaning three extraction cycles were performed. The supernatants were combined and concentrated in vacuo to about 20% of the original volume to form a concentrate that was sterile filtered (0.2 micron filter) to form the crude extract, which was then diluted with 50% aqueous ethanol. The content of water, ethanol, and other components in the crude extract was determined. The content of oleandrin in the crude extract was about 1-5 mg/mL of extract.

As used herein, the term "about" or "approximately" are taken to mean ±10%, +5%, +2.5% or 11% of a specified valued. As used herein, the term "substantially" is taken to mean "to a large degree" or "at least a majority of" or "more than 50% of".

The above is a detailed description of particular embodiments of the invention. It will be appreciated that, although specific embodiments of the invention have been described herein for purposes of illustration, various modifications may be made without departing from the spirit and scope of the invention. Accordingly, the invention is not limited except as by the appended claims. All of the embodiments disclosed and claimed herein can be made and executed without undue experimentation in light of the present disclosure.

The invention claimed is:

1. An oleandrin-containing combination composition comprising a portion of oleandrin-containing organic solvent extract and a portion of oleandrin-containing SbCL (subcritical liquid) extract, wherein the organic solvent extract was prepared by extraction with alcohol or alcohol and water, and the SbCL extract was prepared by extraction with carbon dioxide or carbon dioxide and alcohol.

2. The combination composition of claim 1, wherein a) the compositional profile of extracted volatile and semi-volatile components in said organic solvent extract is different than the compositional profile of said components in said subcritical liquid extract; and/or b) relative to oleandrin content, the subcritical liquid extract comprises a greater proportion of extracted volatile and semi-volatile components than does the organic solvent extract.

3. The combination composition of claim 1, wherein said composition comprises oleandrin and one or more compounds selected from the group consisting of one or more cardiac glycosides, one or more glycone constituents of cardiac glycosides, glucoside, fructoside, glucuronide, one or more aglycones, one or more glycoside precursors, cardenolides, cardadienolides, cardatrienolides, one or more steroids, one or more triterpenes, one or more saccharides, one or more polysaccharides, one or more alkaloids, one or more proteins, fat, one or more other non-cardiac glycoside therapeutically effective agent, and any combination thereof.

4. A pharmaceutical composition comprising at least one pharmaceutical excipient and the combination composition of claim 1.

5. A method of treating or preventing a condition, disease or disorder that is therapeutically responsive to oleandrin, the method comprising administering to a subject in need thereof one or more doses of said pharmaceutical composition of claim 4, thereby treating or preventing said condition, disease or disorder.

6. A method of treating or preventing a condition, disease or disorder that is therapeutically responsive to oleandrin, the method comprising administering to a subject in need thereof one or more doses of the combination composition of claim 1, thereby treating or preventing said condition, disease or disorder.

7. The combination composition of claim 1, wherein the SbCL extract is produced by a method comprising
   subjecting oleandrin-containing biomass to subcritical liquid extraction (SbCLE) employing SbCL, comprising carbon dioxide, for a period of time sufficient to extract the oleandrin and form extraction milieu;
   separating said biomass from said extraction milieu to provide oleandrin-containing SbCL; and
   removing SbCL from said oleandrin-containing SbCL to provide said oleandrin-containing extract (OCE).

8. The combination composition of claim 7, wherein the method further comprises one or more of the following steps: a) separating said biomass from the extraction milieu by filtering the extraction milieu; b) adding modifier to the carbon dioxide or extraction milieu; c) heating and pressurizing the interior of a vessel containing the extraction milieu to form subcritical liquid phase extraction milieu; d) removing said SbCL from said oleandrin-containing SbCL by volatilizing said SbCL to form raw SbCL extract; e) diluting the raw SbCL extract with organic solvent or aqueous organic solvent; f) filtering the diluted raw or crude SbCL extract one or more times; g) treating the diluted raw or crude SbCL extract with activated carbon; h) removing most of the organic solvent from the diluted raw extract to form; and/or i) sterile filtering the raw or crude extract to obtain the SbCL extract.

9. The combination composition of claim 7, wherein the SbCL comprises carbon dioxide and one or more modifiers.

10. The combination composition of claim 9, wherein the one or more modifiers is alcohol.

11. The combination composition of claim 7, wherein the carbon dioxide, along with any modifier, if any is present, is in the subcritical liquid phase during about 50% or more of the extraction time period.

12. The combination composition of claim 11, wherein the extraction milieu, comprising extraction fluid, carbon dioxide along with any modifier, if any is present, in the subcritical liquid phase and biomass, remains in liquid form for at least 60% of the extraction period.

13. The combination composition of claim 7, wherein, with respect to the phase diagram of $CO_2$, the SbCLE is conducted a) at or below the critical pressure ($p_c$), below the critical temperature ($t_c$), and above the liquid-gas phase line; b) at or below the $t_c$ and below the $p_c$, and above the liquid-gas phase line; c) at or above the $p_c$, below the $t_c$, above the liquid-gas phase line, and below the solid-liquid phase line; or d) at a temperature and pressure falling within the liquid region bounded by the solid-liquid phase line, the liquid-gas phase line, the liquid-supercritical phase line, the triple point (solid-liquid-gas) temperature ($t_{tp}$), the triple point pressure ($p_{tp}$), the critical point (liquid-gas-supercritical) temperature ($t_{cp}$), and the critical point pressure ($p_{cp}$).

14. The combination composition of claim 7, wherein the SbCLE is conducted at a temperature of about temperature of about 0° C. up to about 31° C. and a pressure of about 5.2 bar to about 3000 bar.

15. The combination composition of claim 7, wherein the weight ratio of extraction liquid, comprising carbon dioxide and optionally further comprising modifier, to biomass is in the range of about 20:1 to about 100:1, based on weight of both the solvent and the raw material.

16. The combination composition of claim 9, wherein the weight ratio of carbon dioxide to modifier is in the range of about 100:about 0.01-20.

17. The combination composition of claim 7, wherein a) independently upon each occurrence, the biomass is dehydrated, dehumidified, freeze-dried, and/or desiccated prior to extraction; b) independently upon each occurrence, the biomass is dried prior to extraction; c) independently upon each occurrence, the biomass is not dehydrated prior to extraction; or d) independently upon each occurrence, the biomass is not dried prior to extraction.

18. A method of producing an oleandrin-containing combination composition, the method comprising
    subjecting oleandrin-containing first biomass to organic solvent extraction by forming an extraction milieu and thereby to provide an oleandrin-containing organic solvent extract;
    subjecting oleandrin-containing second biomass to subcritical liquid (SbCL) extraction (SbCLE) to provide an oleandrin-containing SbCL extract; and
    combining said oleandrin-containing organic solvent extract and said oleandrin-containing SbCL extract to provide said oleandrin-containing combination composition.

19. The method of claim 18, wherein a) said organic solvent extraction is conducted with organic solvent or aqueous organic solvent; b) independently upon each occurrence, said organic solvent or aqueous organic solvent comprises alcohol; c) independently upon each occurrence, said organic solvent is selected from the group consisting of methanol, ethanol, propanol, butanol, chloroform, methylene chloride, ethyl acetate, and a combination thereof; d) said organic solvent extraction comprises extracting said oleandrin-containing biomass with organic solvent or aqueous organic solvent one or more times; e) independently upon each occurrence, said aqueous organic solvent comprises up to about 20% w/w, about 5% w/w to about 15% w/w, or about 10% w/w of water; f) said organic solvent extract is conducted at a temperature of from about 0° C. to about 75° C., about 5° C. to about 70° C., about 10° C. to about 60° C., about 10° C. to about 50° C., about 10° C. to about 45° C., or about 20° C. to about 40° C.; g) the v/w ratio of organic solvent to biomass or of aqueous organic solvent to biomass is in the range of about 50-1:about 1, about 40-1:about 1, about 30-1:about 1, about 20-1:about 1, about 20-5:about 1, or about 10:about 1.

20. The method of claim 18, wherein the organic solvent extraction further comprises one or more of the following: a) separating said biomass from the extraction milieu by filtering the extraction milieu to form the extract; b) adding aqueous liquid to the organic solvent or extraction milieu; c) reducing the content of organic solvent from said extract; d) treating the extract with activated carbon; e) filtering the extract one or more times; f) adding additional organic solvent to the extract; g) sterile filtering the organic solvent extract; and/or h) adding water to the extract to form aqueous extract and extracting the aqueous extract with organic solvent.

21. The combination composition of claim 15, wherein a) prior to extraction the water content in the biomass is about 20 wt % or less; b) prior to extraction the biomass has a particle size d0.5 of less than about 1", less than about 0.75", less than about 0.5", less than about 0.4", less than about 0.3", less than about 0.2", less than about 0.1", less than about 0.05", or less than about 0.01", said particle being with respect to ASTM sieve mesh opening size; and/or c) the oleandrin-containing biomass is *Nerium* sp., *Nerium oleander*, *Nerium oleander* L, *Nerium odourum*, white oleander, pink oleander, *Thevetia* sp., *Thevetia peruviana*, yellow oleander, *Thevetia nerifolia*, *Agrobacterium tumefaciens* transformed and elicited in *Nerium* sp., cell culture, or a combination thereof.

22. The combination composition of claim 1, wherein the composition comprises at least oleandrin, oleanolic acid, ursolic acid, betulinic acid, kanerocin, kanerodione, oleandrigenin, *Nerium* F, neritaloside, odoroside A, and odoroside H, adynerin, odoroside-G-acetate, and gitoxigenin.

23. The combination composition of claim 22, wherein a) in the organic solvent extract, the relative contents of compounds is kanerocin>kanerodione>oleanolic acid>ursolic acid~oleandrin~betulinic acid>oleandri- genin-~*Nerium* F, odoroside A, odoroside H~adynerin~odoroside-G-acetate>gitoxigenin; and b) in the SbCL extract, the relative contents of compounds is oleanolic acid>ursolic acid~oleandrin~betulinic acid>oleandrigenin~*Nerium* F>odoroside A, odoroside H~adynerin~odoroside-G-acetate>kanerocin.

24. The combination composition of claim 22 further comprising one or more of neriin, folinerin, gitoxigenin, digitoxigenin, nerigoside, rutin, ursonic acid, neridienone A, adynerigenin, deacetyloleandrin, odoroside G acetate, and/or quercetin.

25. The combination composition of claim 22 further comprising one or more polyphenol(s), one or more carbohydrate(s), one or more flavonoid(s), one or more amino acid(s), one or more soluble protein(s), one or more cellulose(s), one or more starch(es), one or more alkaloid(s), one or more saponin(s), one or more tannin(s), or any combination thereof.

26. The combination composition of claim 22 wherein a) in the organic solvent extract made by ethanolic extraction, the relative content of components is total free amino acids>total sugars>total cellulose>total alkaloids>total polyphenols~total flavonoids>total starch>total crude protein; b) in the organic solvent extract made by aqueous ethanolic extraction, the relative content of components is total free amino acids>total cellulose>total alkaloids>total sugars>total polyphenols~total flavonoids>total starch>total crude protein; or c) in the SbCL extract, the relative content of components is total free amino acids>total starch>total alkaloids>total cellulose>total flavonoids>total sugars>total polyphenols>total crude protein.

27. The combination composition of claim 1, wherein the composition is included in a pharmaceutical composition, nutraceutical composition, cosmeceutical composition, or dosage form.

28. The combination composition of claim 7, wherein a) prior to extraction the water content in the biomass is about 20 wt % or less; b) prior to extraction the biomass has a particle size d0.5 of less than about 1", less than about 0.75", less than about 0.5", less than about 0.4", less than about 0.3", less than about 0.2", less than about 0.1", less than about 0.05", or less than about 0.01", said particle being with respect to ASTM sieve mesh opening size; and/or c) the oleandrin-containing biomass is *Nerium* sp., *Nerium oleander, Nerium oleander* L, *Nerium odourum*, white oleander, pink oleander, *Thevetia* sp., *Thevetia peruviana, yellow oleander, Thevetia nerifolia, Agrobacterium tumefaciens* transformed and elicited in *Nerium* sp., cell culture, or a combination thereof.

29. An oleandrin-containing combination composition produced according to the method of claim 18.

* * * * *